United States Patent

Natsume et al.

(10) Patent No.: US 9,802,312 B2
(45) Date of Patent: Oct. 31, 2017

(54) OPERATION COMMAND GENERATION DEVICE, OPERATION COMMAND GENERATION METHOD, NON-TRANSITORY COMPUTER READABLE STORAGE MEDIUM, AND PROCESS SYSTEM

(71) Applicants: NATIONAL INSTITUTE OF ADVANCED INDUSTRIAL SCIENCE AND TECHNOLOGY, Tokyo (JP); Kabushiki Kaisha Yaskawa Denki, Kitakyushu-shi (JP); Robotic Biology Institute Inc., Tokyo (JP)

(72) Inventors: Toru Natsume, Zushi (JP); Takashi Nagasaki, Kitakyushu (JP); Makoto Umeno, Kitakyushu (JP); Tatsuro Ipposhi, Kitakyushu (JP); Hirokazu Kariyazaki, Kitakyushu (JP)

(73) Assignees: NATIONAL INSTITUTE OF ADVANCED INDUSTRIAL SCIENCE AND TECHNOLOGY, Tokyo (JP); KABUSHIKI KAISHA YASKAWA DENKI, Fukuoka (JP); ROBOTIC BIOLOGY INSTITUTE INC., Tokyo (JP)

( * ) Notice: Subject to any disclaimer, the term of this patent is extended or adjusted under 35 U.S.C. 154(b) by 0 days.

(21) Appl. No.: 14/945,435

(22) Filed: Nov. 19, 2015

(65) Prior Publication Data

US 2016/0144507 A1 May 26, 2016

(30) Foreign Application Priority Data

Nov. 21, 2014 (JP) ................................ 2014-237200

(51) Int. Cl.
G06F 7/00 (2006.01)
B25J 9/16 (2006.01)
G01N 35/00 (2006.01)

(52) U.S. Cl.
CPC ........... *B25J 9/1628* (2013.01); *B25J 9/1656* (2013.01); *B25J 9/1679* (2013.01);
(Continued)

(58) Field of Classification Search
USPC ....................................................... 700/214
See application file for complete search history.

(56) References Cited

U.S. PATENT DOCUMENTS 5,841,959 A 11/1998 Guiremand
5,930,461 A * 7/1999 Bernstein ............... B25J 9/1671
700/247

(Continued)

FOREIGN PATENT DOCUMENTS

EP 0496785 A1 8/1992
JP 2005-121476 A 5/2005

(Continued)

OTHER PUBLICATIONS

European Search Report dated Apr. 13, 2016 for corresponding EP application No. 15195512.7.

(Continued)

*Primary Examiner* — Kyle Logan
(74) *Attorney, Agent, or Firm* — Hubbs, Enatsky & Inoue PLLC

(57) ABSTRACT

Provided is an operation command generation device configured to generate an operation command, which is a collection of jobs to be carried out by a process system including a robot based on a protocol chart including a process symbol representing a process to be carried out on a container containing a process subject, the operation (Continued)

command generation device including: a process job generation unit configured to generate, based on the process symbol, a job for causing the process system to carry out the process on the container at a work area; and a transfer job generation unit configured to generate, when the process represented by the process symbol is not a process to be carried out on the same container, a job to transfer the container from the work area to a retreat area after the process represented by the process symbol has been carried out.

13 Claims, 23 Drawing Sheets

(52) U.S. Cl.
CPC ............... *G01N 35/0092* (2013.01); *G05B 2219/40113* (2013.01); *G05B 2219/45092* (2013.01)

(56) References Cited

U.S. PATENT DOCUMENTS

| | | |
|---|---|---|
| 6,594,537 B1 | 7/2003 | Bernstein et al. |
| 2003/0004612 A1 | 1/2003 | Domanico et al. |
| 2004/0208795 A1* | 10/2004 | Toi ................... G01N 35/1011 422/400 |
| 2007/0048863 A1 | 3/2007 | Rodgers et al. |
| 2010/0202024 A1* | 8/2010 | Carey ............. G05B 19/41865 358/3.28 |

FOREIGN PATENT DOCUMENTS

| | | |
|---|---|---|
| JP | 2009-502168 A | 1/2009 |
| JP | 2010-127681 A | 6/2010 |
| JP | 2011-033395 A | 2/2011 |
| JP | 2012-117880 A | 6/2012 |

OTHER PUBLICATIONS

European Search Report dated Apr. 7, 2016 for corresponding EP application No. 15195511.9.
PCT/ISA/237 of Dec. 22, 2016, International Application No. PCT/JP2014/080984 and Partial translation thereof.
The Office Action of Dec. 29, 2016, for corresponding U.S. Appl. No. 14/945,437.
Computer generated English translation of Japanese Application No. 2005-121476A, previously submitted with the IDS dated Mar. 21, 2017.

* cited by examiner

OPERATION COMMAND GENERATION DEVICE, OPERATION COMMAND GENERATION METHOD, NON-TRANSITORY COMPUTER READABLE STORAGE MEDIUM, AND PROCESS SYSTEM

INCORPORATION BY REFERENCE

The present disclosure contains subject matter related to that disclosed in Japanese Priority Patent Application JP 2014-237200 filed in the Japan Patent Office on Nov. 21, 2014, the entire contents of which are hereby incorporated by reference.

BACKGROUND OF THE INVENTION

Field of the Invention

The present invention relates to an operation command generation device, an operation command generation method, a non-transitory computer-readable storage medium, and a process system.

Description of the Related Art

In the fields of biochemistry and biotechnology, a work procedure and conditions of the operations to be carried out on a process subject, such as a series of inspections, cultivation, and amplification (hereinafter, these operations are collectively referred to as "experiment"), are commonly referred to as a protocol. A protocol is the information required in order to obtain a result that is reproducible for an experiment or to verify the experiment result.

Further, it is desired that experiments performed in the above-mentioned fields exclude as much as possible factors that may have an adverse impact on the experiment result, such as contamination.

SUMMARY OF THE INVENTION

According to one aspect of the present invention, there is provided an operation command generation device configured to generate an operation command, which is a collection of jobs to be carried out by a process system including at least a robot based on a protocol chart including at least a process symbol representing a process to be carried out on a container containing a process subject, the operation command generation device including: a process job generation unit configured to generate, based on the process symbol, a job for causing the process system to carry out the process on the container at a work area; and a transfer job generation unit configured to generate, when the process represented by the process symbol is not a process to be carried out on at least the same container, a job for causing the process system to transfer the container from the work area to a retreat area after the process represented by the process symbol has been carried out.

Further, according to another aspect of the present invention, there is provided an operation command generation method for generating an operation command, which is a collection of jobs to be carried out by a process system including at least a robot based on a protocol chart including at least a process symbol representing a process to be carried out on a container containing a process subject, the operation command generation method including: generating, based on the process symbol, a job for causing the process system to carry out the process on the container at a work area; and generating, when the process represented by the process symbol is not a process to be carried out on at least the same container, a job for causing the process system to transfer the container from the work area to a retreat area after the process represented by the process symbol has been carried out.

DESCRIPTION OF THE EMBODIMENTS

Based on the knowledge of the inventors of the present invention, the likelihood of an anticipated result being obtained in a biochemistry or biotechnology experiment, that is, the reproducibility of the experiment, largely depends on the competence of the person conducting the experiment, which can in some cases hinder verification of the reliability of the experiment result, for example. Accordingly, the inventors investigated excluding human factors by using a robot to carry out the experiment.

In this case, in order to prevent contamination and the like, and to improve the ease with which a person can grasp the operations of a robot that he/she has observed, the robot needs to be made to carry out operations that may not necessarily be explicitly indicated in the protocol.

Therefore, the inventors of the present invention invented a novel and creative operation command generation device and the like by carrying out diligent research and development into preventing contamination and the like, and automatically generating an operation command for causing a robot to perform an experiment based on a protocol. This operation command generation device and the like are described below using an embodiment as an example.

Figure 1:
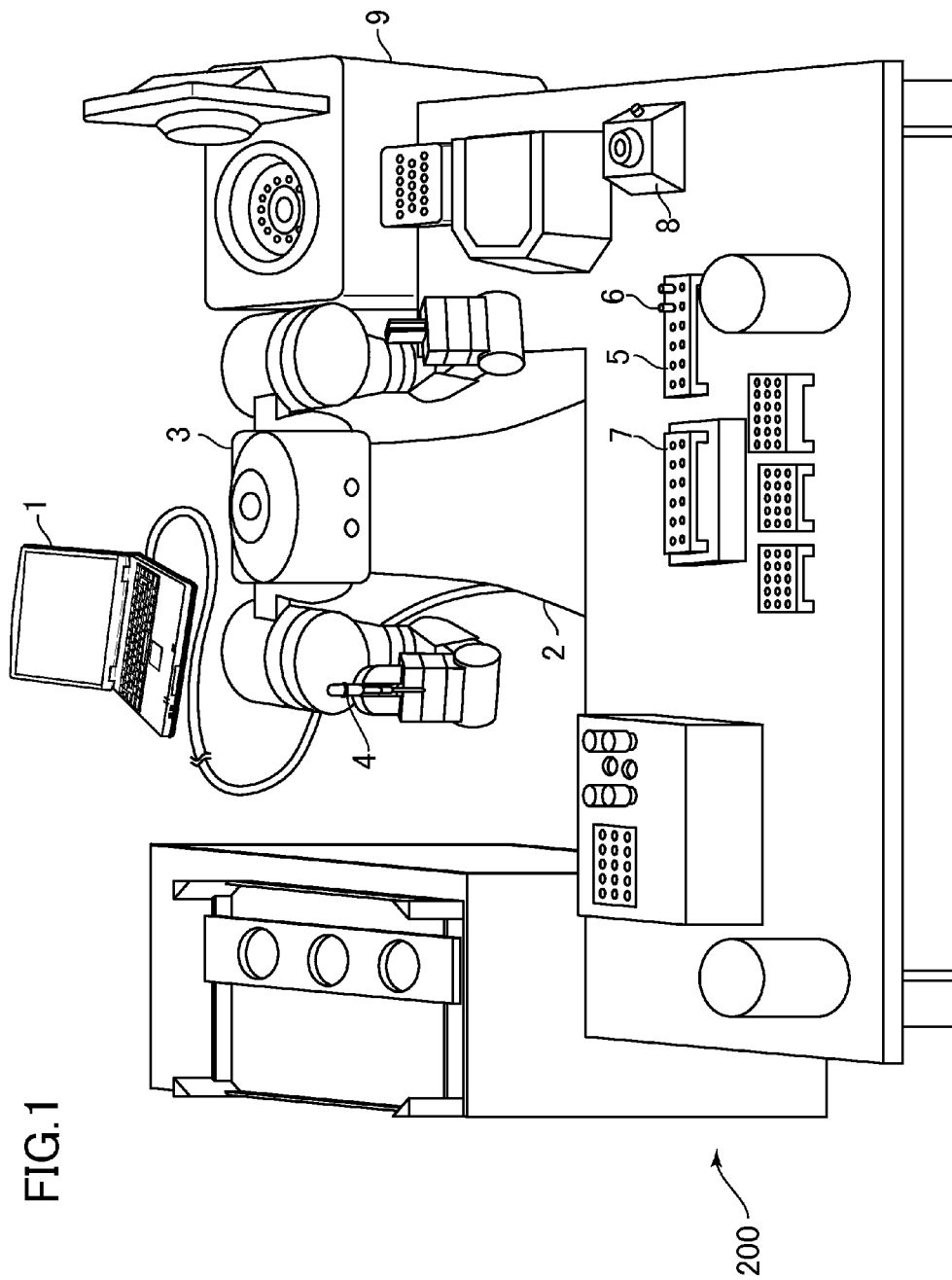
FIG. 1 is a schematic diagram for illustrating a physical configuration of a process system according to an embodiment of the present invention.

FIG. 1 is a schematic diagram for illustrating an example of a physical configuration of a process system 200 according to one embodiment of the present invention. The process system 200 includes an operation command generation device 1 configured to generate an operation command for a robot 3 based on a protocol chart showing a protocol, a robot controller 2 configured to control the robot 3 based on the generated operation command, and the robot 3, which is controlled by the robot controller 2 and is configured to execute an experiment. The operation command generation device 1 itself may be a dedicated device. However, in this case, the operation command generation device 1 is realized by using a common computer. In other words, a commercially-available computer configured to execute a computer program for causing the computer to operate as the operation command generation device 1 is used for the operation command generation device 1. The computer program is in general provided in the form of application software, and is used when installed on the computer. The application software may be provided by recording the application software on a compact disc read-only memory (CD-ROM), a digital versatile disc (DVD) ROM, or another suitable computer-readable information recording medium. Further, the application software may be provided over various information communication networks, such as the Internet. In addition, the functions of the application software may be provided by a server at a remote location over an information communication network, that is, be realized by so-called cloud computing. Still further, the robot controller 2 may be integrated with the robot 3, or in a stand-alone manner. The robot controller 2 causes the robot 3 to execute a desired operation based on an operation command generated by the operation command generation device 1.

The robot 3 is an articulated dual-arm robot that is configured to carry out processes on a container containing a process subject. The robot 3 is capable of manipulating a piece of experiment equipment (which may or may not be shown) such as grasping and manipulating a pipette 4 with an arm. Further, the robot 3 is capable of moving various containers (which may or may not be shown) such as grasping a microtube 6 arranged in a subrack 5 and moving the microtube 6 from the subrack 5 to a main rack 7 or the like. In this embodiment, when the robot 3 is carrying out a process on the microtube 6, such as injecting the process subject into the microtube 6, the robot 3 moves the microtube 6 to the main rack 7, and carries out the process above the main rack 7. The process system 200 also includes an agitator 8 and a centrifugal separator 9. In the example illustrated in FIG. 1, one example of a piece of equipment to be used when the robot 3 performs the experiment is illustrated. However, the process system 200 may also include other equipment. For example, the process system 200 may include a thermostatic bath, a magnet rack, and the like. Further, the robot 3 is not limited to the type that is illustrated, and the robot 3 may be a single-arm robot or the like. In addition, the robot 3 may be configured from a plurality of robots working together.

Figure 2:
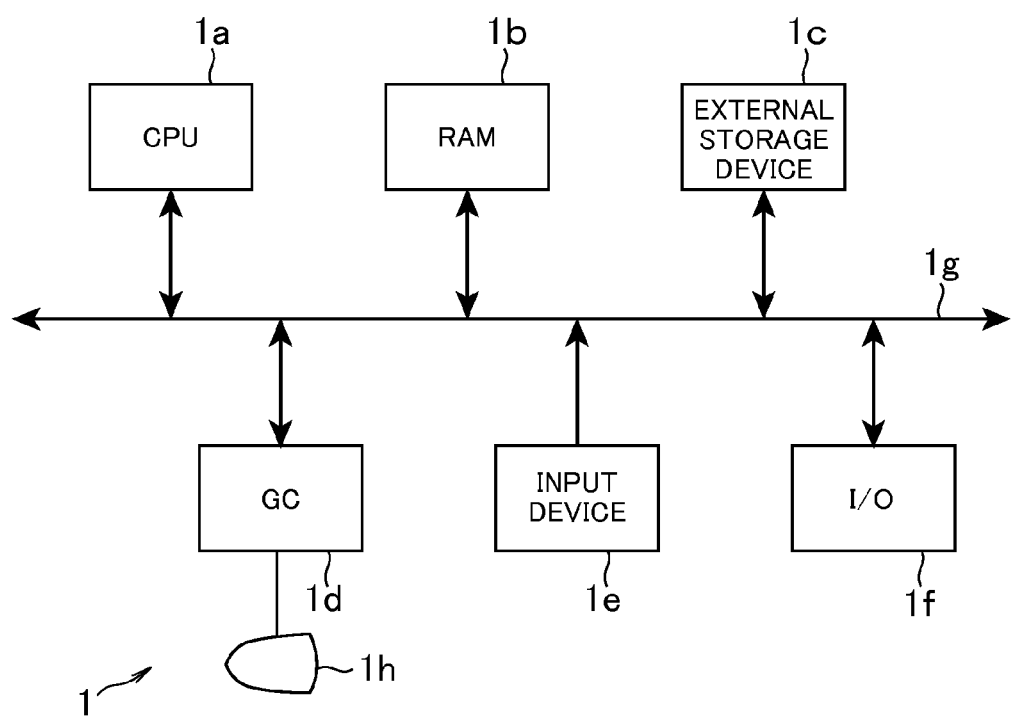
FIG. 2 is a configuration block diagram for illustrating a physical configuration of an operation command generation device according to the embodiment of the present invention.

FIG. 2 is a block diagram for illustrating a physical configuration of the operation command generation device 1 according to the embodiment of the present invention. The configuration illustrated in FIG. 2 is a general computer used as the operation command generation device 1. In the computer, a central processing unit (CPU) $1a$, a random access memory (RAM) $1b$, an external storage device $1c$, a graphics controller (GC) $1d$, an input device $1e$, and an input/output (I/O) $1f$ are connected to one another by a data bus $1g$ so that the devices can exchange electric signals therebetween. In this case, the external storage device $1c$ is a device capable of statically recording information, such as a hard disk drive (HDD) or a solid state drive (SSD). Further, signals from the GC $1d$ are output and displayed as an image on a monitor $1h$, such as a flat panel display, by which the user visually recognizes the image. The input device $1e$ is a device, such as a keyboard, a mouse, or a touch panel, by which the user inputs information. The I/O $1f$ is an interface that allows the operation command generation device 1 to exchange information with an external device.

Figure 3:
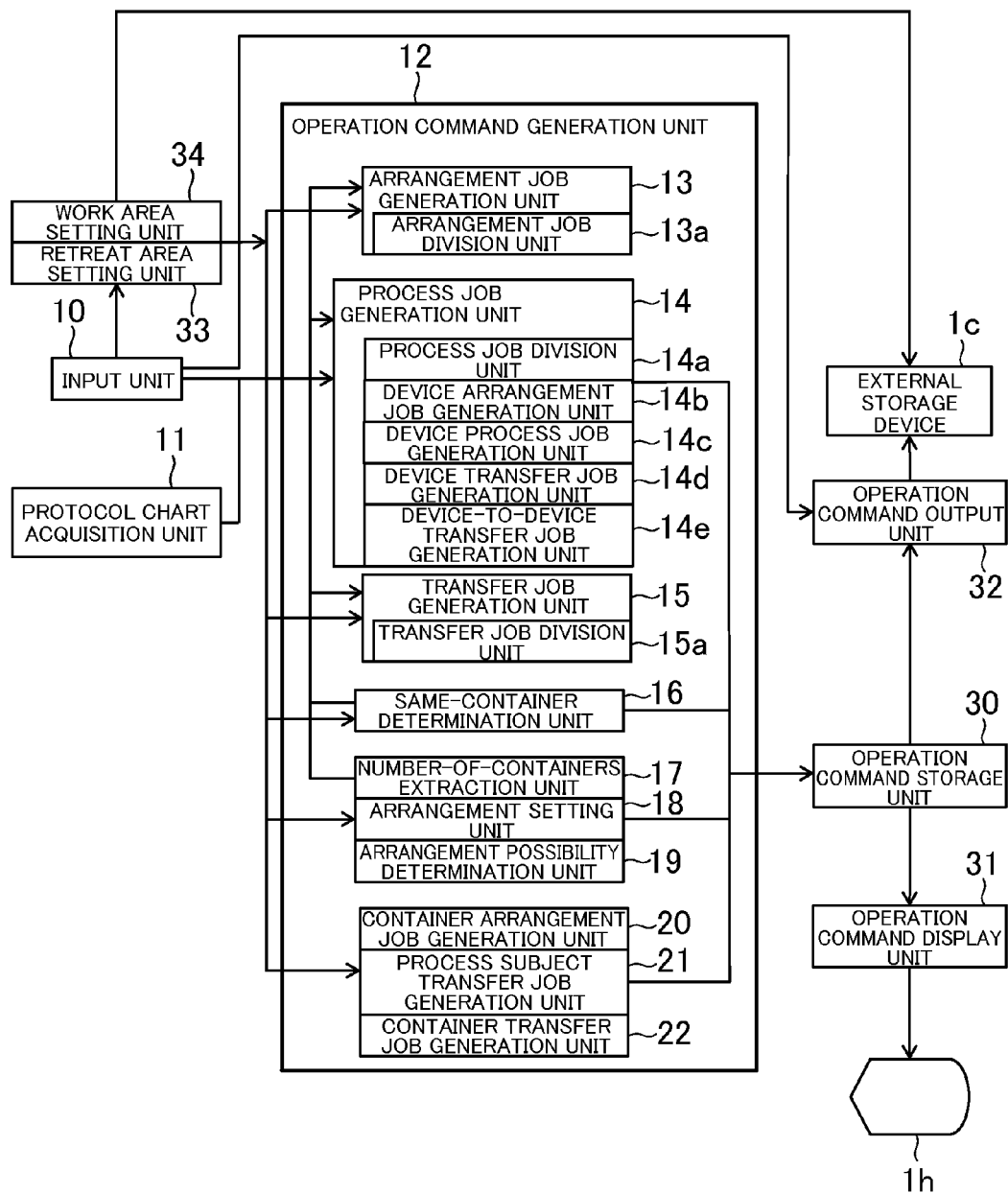
FIG. 3 is a function block diagram of the operation command generation device according to the embodiment of the present invention.

FIG. 3 is a function block diagram of the operation command generation device 1 according to this embodiment. Note that, the function blocks illustrated in FIG. 3 focus on the functions that the operation command generation device 1 has. It is not necessary to have a physical configuration in which the each function corresponds to a function block on a one-to-one basis. Some function blocks may be realized by an information processing device, such as the CPU $1a$ of the operation command generation device 1, executing specific software. Further, some function blocks may be realized by a specific storage area being allocated to an information storage device, such as the RAM 1b of the operation command generation device 1.

The operation command generation device 1 includes an input unit 10 configured to receive various inputs from a user, and a protocol chart acquisition unit 11 configured to acquire a protocol chart showing a protocol. Further, the operation command generation device 1 includes an operation command generation unit 12 configured to generate an operation command based on the inputs received by the input unit 10 and the protocol chart acquired by the protocol chart acquisition unit 11. In addition, the operation command generation device 1 includes an operation command storage unit 30 configured to store electronic data of the operation command currently being generated and operation commands that have been generated, an operation command display unit 31 configured to form the electronic data of the operation commands stored in the operation command storage unit 30 and display the formed electronic data on the monitor 1h, and an operation command output unit 32 configured to output the generated operation command as an electronic file in a format that can be read by the robot. The operation command generation device 1 also includes, based on the inputs received by the input unit 10, a retreat area setting unit 33 configured to set a retreat area, which is an area to which the container temporarily retreats, from among the container storage areas included in the process system, and a work area setting unit 34 configured to set a work area, which is an area in which the robot 3 carries out a process on the container, from among the container storage areas included in the process system. Setting information set by the retreat area setting unit 33 and the work area setting unit 34 is stored in an area setting storage unit 35, and is input to the operation command generation unit 12.

The input unit 10 is normally configured by the input device 1e illustrated in FIG. 2. However, when the operation command generation device 1 is an application server used in cloud computing, the I/O 1f into which operation information input by the user on a terminal at a remote location is input corresponds to the input unit 10.

The operation command generation unit 12 includes various function blocks for generating the operation command. Details of those function blocks are described below in conjunction with the description of the generation procedure of the operation command. In this embodiment, the operation command generation unit 12 includes an arrangement job generation unit 13 configured to generate a job for causing the process system 200 to move the container containing the process subject from the retreat area and arrange the container in the work area. Further, the operation command generation unit 12 includes a process job generation unit 14 configured to generate, based on a process symbol, a job for causing the process system 200 to carry out a process on the container at the work area. In addition, the operation command generation unit 12 includes a transfer job generation unit 15 configured to generate, when the process represented by the process symbol is not a process to be carried out on at least the same container, a job for causing the process system 200 to transfer the container from the work area to the retreat area after the process represented by the process symbol has been carried out. Still further, the operation command generation device 1 includes a same-container determination unit 16 configured to determine whether or not a plurality of process symbols represent processes to be carried out on the same container, and a number-of-containers extraction unit 17 configured to extract, based on a protocol chart, the number of containers associated with the process symbol. The operation command generation device 1 also includes an arrangement setting unit 18 configured to set an arrangement of the containers in the work area for the number of containers extracted by the number-of-containers extraction unit 17 so that the containers are not duplicately arranged in the same storage area, and an arrangement possibility determination unit 19 configured to determine whether or not all of the number of containers extracted by the number-of-containers extraction unit 17 can be arranged in a first range of the work area. Further, the operation command generation device 1 includes a container arrangement job generation unit 20 configured to generate a job for causing the process system 200 to arrange a first container containing the process subject in a transfer source range, and arrange a second container in a transfer destination range. In addition, the operation command generation device 1 includes a process subject transfer job generation unit 21 configured to generate, based on a transfer symbol contained in the protocol chart, a job for causing the process system 200 to transfer the process subject from the first container to the second container, and a container transfer job generation unit 22 configured to generate a job, which is to be carried out after the transfer of the process subject, for causing the process system 200 to transfer the first container from the transfer source range to the retreat area, and a job, which is to be carried out after the transfer of the process subject, for causing the process system 200 to transfer the second container from the transfer destination range to the retreat area.

Note that, in this specification, the term job refers to a command, which is issued to a process system including at least a robot, for carrying out a unit process on a container containing a process subject. Further, the term operation command refers to a collection of jobs that combines a plurality of jobs. The operation command generation device 1 is configured to generate jobs, which are unit processes, based on process symbols and the like represented in a protocol chart, and combine the generated jobs to generate an operation command for the process system.

The arrangement job generation unit 13 further includes an arrangement job division unit 13a configured to divide, when it is determined by the arrangement possibility determination unit 19 that not all of the containers can be arranged in the first range of the work area, a job for arranging the containers into two or more jobs for causing the process system 200 to arrange in the first range the number of containers that can be arranged in the first range.

Further, the process job generation unit 14 also includes a process job division unit 14a configured to divide, when it is determined by the arrangement possibility determination unit 19 that not all of the containers can be arranged in the first range of the work area, based on the process symbol, a job for causing the process system 200 to carry out the process represented by the process symbol into two or more jobs to be each carried out on the number of containers that can be arranged in the first range. In addition, the process job generation unit 14 includes a device arrangement job generation unit 14b configured to generate a job for arranging the container from the work area in a peripheral device, and a device process job generation unit 14c configured to generate, based on the process symbol, a job for causing the process system 200 to carry out the process using a peripheral device on the container. Still further, the process job generation unit 14 includes a device transfer job generation unit 14d configured to generate, when the process represented by the process symbol is not a process to be carried out on at least the same container, a job for causing the process system 200 to transfer the container from the peripheral device to the work area after the process represented by the process symbol has been carried out. The process job generation unit 14 also includes a device-to-device transfer job generation unit 14e configured to generate a job to be carried out between a process using a first peripheral device and a process using a second peripheral device, the processes being represented by a plurality of the process symbols, the job causing the process system 200 to transfer the container from the first peripheral device to the second peripheral device.

The transfer job generation unit 15 includes a transfer job division unit 15a configured to divide, when it is determined by the arrangement possibility determination unit 19 that not all of the containers can be arranged in the first range, a job for causing the process system 200 to transfer the container into two or more jobs based on the division carried out by the above-mentioned process job division unit.

Figure 4:
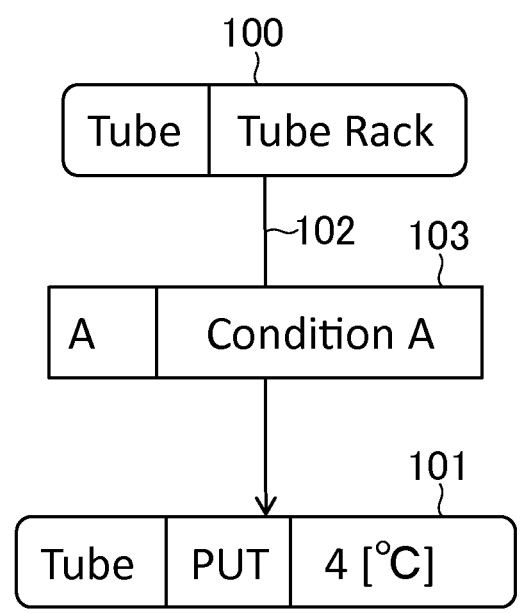
FIG. 4 is a diagram for illustrating a first example of a protocol chart acquired by the operation command generation device according to the embodiment of the present invention.

FIG. 4 is a diagram for illustrating a first example of the protocol chart acquired by the operation command generation device 1 according to this embodiment.

In this specification, the term protocol chart refers to a diagram that is shown in a manner that allows a protocol to be visually understood, and the term protocol refers to the work procedure and conditions of a pre-process and the like to be carried out on a process subject in the field of biochemistry or biotechnology. The protocol chart includes at least a process symbol representing a process to be carried out on a container containing the process subject. Further, the term process subject refers to a specimen on which an experiment in the above-mentioned fields is to be performed. In general, the process subject is often a portion of biological tissue, such as a cell, DNA, or the like. The experiment is generally carried out by placing the process subject in a piece of equipment that is particularly suited to the experiment, such as a microtube (centrifuge tube), a Petri dish, or a microplate (microtiter plate). However, when the term container is used by itself in this specification, the term refers to all of those pieces of equipment suitable for containing the process subject in the experiment.

Further, for convenience, the upward direction in FIG. 4 is referred to as a first direction, and the direction intersecting the first direction is referred to as a second direction. It is not necessary for the angle of intersection between the first direction and the second direction to be a right angle. However, in this case, the first direction and the second direction are perpendicular to each other. As a result, the second direction is the axis in the horizontal direction in FIG. 4.

In the protocol chart of this example, basically, an initial symbol 100 representing an initial state of the container containing the process subject and a final symbol 101 representing a final state of the container are arranged in the first direction. The initial symbol 100 and the final symbol 101 are connected in the first direction by a procedure line 102 heading from the initial symbol 100 to the final symbol 101. A process symbol 103 representing an individual process to be carried out on the container is arranged along the procedure line 102. In the first example illustrated in FIG. 4, there is a set of the initial symbol 100 and final symbol 101 in which "Tube" is written and the procedure line 102 connecting the initial symbol 100 and the final symbol 101. In this case, the procedure line 102 represents the procedure to be carried out by the process as an arrow line. In other words, the protocol chart of this example means that first the job represented by the initial symbol 100, in which "Tube" is written, is carried out, then the job represented by the process symbol 103, in which "A" is written for "Tube", is carried out, and lastly the job represented by the final symbol 101, in which "Tube" is written, is carried out.

Note that, in the protocol chart of this example and the protocol charts of the second example to the fifth example, for ease of explanation, the specific content of the process represented by the process symbol 103 is not exemplified. Examples of the specific content of the process represented by the process symbol 103 include an agitation process carried out by using the agitator 8, a centrifugal separation process carried out by using the centrifugal separator 9, and a reaction process carried out by leaving the container to stand in a thermostatic bath. Further, a process for injecting a drug and the like into the microtube 6 by using the pipette 4 may also be carried out. In addition, when the container is a Petri dish, a scraping process for scraping off cells and the like cultured on a Petri dish by using a spatula may be carried out.

It is now described how the operation command generation device 1 according to this embodiment generates jobs based on the first example of a protocol chart shown in FIG. 4 while preventing contamination and the like.

First, the protocol chart acquisition unit 11 of the operation command generation device 1 acquires the protocol chart. Based on the initial symbol 100, in which "Tube" is written in the topmost level of the protocol chart, the operation command generation unit 12 generates a job for causing the process system 200 to prepare the microtube 6 containing the process subject in the subrack 5. The word "Tube" written on the left side of the initial symbol 100 represents a microtube, and the words "Tube Rack" written on the right side of the initial symbol 100 represent the device in which the microtube is stored, which in this case is a tube rack. Therefore, the operation command generation unit 12 generates a job for moving, by an arm of the robot 3, the microtube from a tube rack to the subrack 5 based on the initial symbol 100 in which "Tube" is written.

Next, the process symbol 103 in which "A" is written, which is connected by the procedure line 102 to the initial symbol 100 in which "Tube" is written, is read. In this case, the process symbol 103 in which "A" is written represents an arbitrary process to be carried out on the microtube based on Condition A. Further, in this case, the area at which the process is to be carried out is not specified in the process symbol 103. However, when a process is carried out on a container at an area in which a different container is arranged, there is a risk of contamination in which a different process subject is mixed into an unintended container. As a result, in principle, the processes to be carried out on the container are performed at the main rack 7.

When the process symbol 103 has been read, the arrangement job generation unit 13 generates a job for causing the process system 200 to transfer the container from the retreat area and arrange the container in the work area. In other words, the arrangement job generation unit 13 generates a job for causing the robot 3 to grasp the microtube 6 with the arm and move the microtube 6 from the subrack 5 to the main rack 7. The arrangement job generation unit 13 inserts the job so that the above-mentioned arrangement operation is carried out before Process A represented by the process symbol.

Further, when the process symbol 103 has been read, the process job generation unit 14 generates, based on the process symbol 103, a job for causing the process system 200 to carry out a process on the container at the work area. In other words, the process job generation unit 14 generates, based on the process symbol 103, a job for carrying out Process A based on Condition A on the microtube 6 at the main rack 7.

In addition, when the process symbol 103 has been read, the transfer job generation unit 15 generates, when the process represented by the process symbol is not a process to be carried out on at least the same container, a job for causing the process system 200 to transfer the container from the work area to the retreat area after the process represented by the process symbol has been carried out. In other words, the transfer job generation unit 15 generates a job for causing the robot 3 to grasp the microtube 6 with the arm and move the microtube 6 from the main rack 7 to the subrack 5. The transfer job generation unit 15 inserts the job so that the above-mentioned transfer operation is carried out after Process A represented by the process symbol.

Thus, with the operation command generation device 1 according to this embodiment, for each process, an operation command can be automatically generated for arranging the microtube 6 placed in the subrack 5 in the main rack 7, carrying out the process at the main rack 7, and when carrying out the process on at least a different container, transferring the microtube 6 to the subrack 5 after the process. When the process is carried out on a different container, contamination and the like can be prevented by transferring the microtube 6 to the subrack 5. Further, when the robot 3 is going to carry out the process on a different container, the person confirming the operations of the robot 3 can clearly confirm that the robot 3 is carrying out an operation for preventing contamination by seeing that the robot 3 transfers the container from the main rack 7 to the subrack 5. In addition, even when for some reason the operation of the robot 3 is stopped midway through an operation in a state in which the container is arranged at the main rack 7, a clear determination regarding which container the process was being carried out on can be made, which facilitates recovery.

Lastly, the operation command generation unit 12 converts the final symbol 101 in which "Tube" is written into a job for causing the process system 200 to carry out the final process on the container. In this case, "PUT" means "to store" in the device, and hence the operation command generation unit 12 generates a job for causing the robot 3 to move the microtube from the subrack 5 and store the microtube in a 4° C. thermostatic bath.

Figure 5:
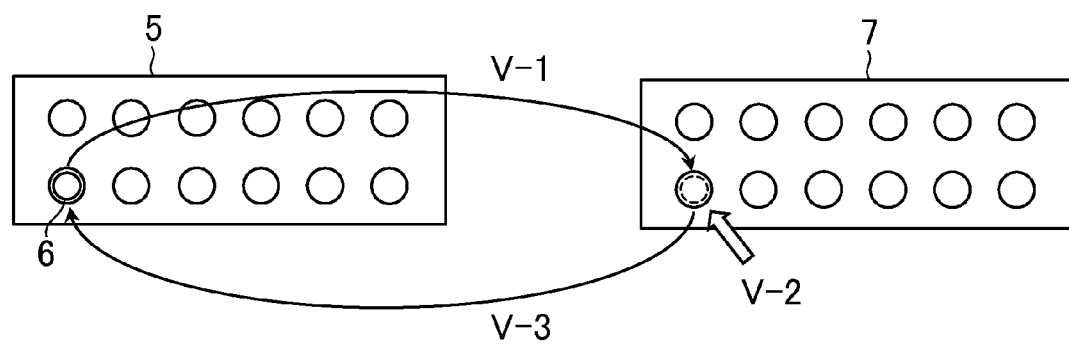
FIG. 5 is a diagram for illustrating operations of a robot in jobs generated based on the first example of the protocol chart.

FIG. 5 is a diagram for illustrating operations of the robot 3 in jobs generated based on the first example of the protocol chart. In FIG. 5, the operations of the robot 3 for three jobs generated based on the process symbol 103 are illustrated using three arrows. FIG. 5 is an illustration of a portion of a work bench when viewed from the robot 3 side (when the robot 3 is arranged beneath the drawing sheet in FIG. 5). Among the 12 storage areas of the subrack 5, the microtube 6 is arranged in the storage area at the lower left of the drawing sheet.

An arrow V-1 indicates an operation of the robot 3 in a job for moving the microtube 6 from the subrack 5, which is the retreat area, and arranging the microtube 6 in the main rack 7, which is the work area. In this example, the main rack 7 and the subrack 5 each have a total of 12 storage areas arranged in two rows of six storage areas. In this case, among the 12 storage areas of the main rack 7, the microtube 6 is arranged in the storage area at the lower left of the drawing sheet. In other words, the microtube 6 is arranged so that the storage area of the microtube 6 in the main rack 7 corresponds to the storage area of the microtube 6 in the subrack 5.

An arrow V-2 indicates an operation of the robot 3 in a job for carrying out Process A on the microtube 6 based on Condition A at the main rack 7, which is the work area. Further, an arrow V-3 indicates an operation of the robot 3 in a job for transferring the microtube 6 from the main rack 7, which is the work area, to the subrack 5, which is the retreat area. In this case, among the 12 storage areas of the subrack 5, the microtube 6 is arranged in the storage area at the lower left of the drawing sheet. In other words, the microtube 6 is returned to the original position at which the microtube 6 was arranged before the preparation operation of the container indicated by the arrow V-1.

With the operation command generation device 1 according to this embodiment, the main rack 7, which is a first storage area, is set by the work area setting unit 34 as the work area, and the subrack 5, which is a second storage area, is set by the retreat area setting unit 33 as the retreat area. Further, the main rack 7 and the subrack 5 included in the process system 200 according to this embodiment are both storage areas capable of storing 12 microtubes. However, the number of containers that can be stored in the first storage area set as the work area and in the second storage area set as the retreat area may be different. The user of the operation command generation device 1 may freely set the retreat area and the work area with the retreat area setting unit 33 and the work area setting unit 34, and may also change the setting of each of the retreat area and the work area for each protocol. Further, the user of the operation command generation device 1 may also set one row of one tube rack as the work area, and may set a row different from the row set as the work area as the retreat area.

Figure 6:
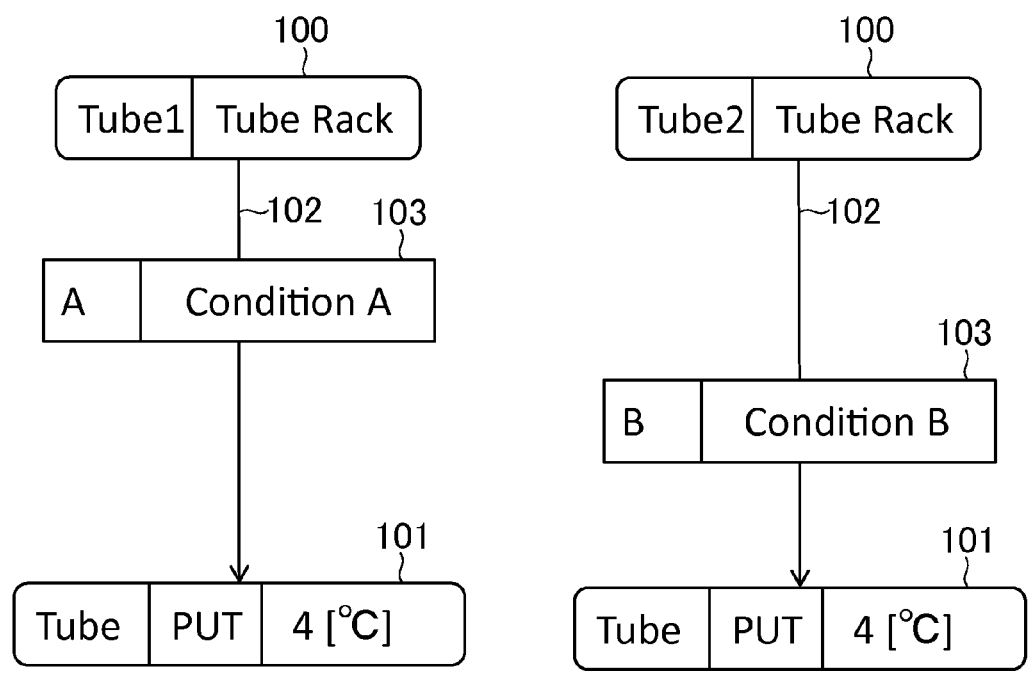
FIG. 6 is a diagram for illustrating a second example of the protocol chart acquired by the operation command generation device according to the embodiment of the present invention.
Figure 7:
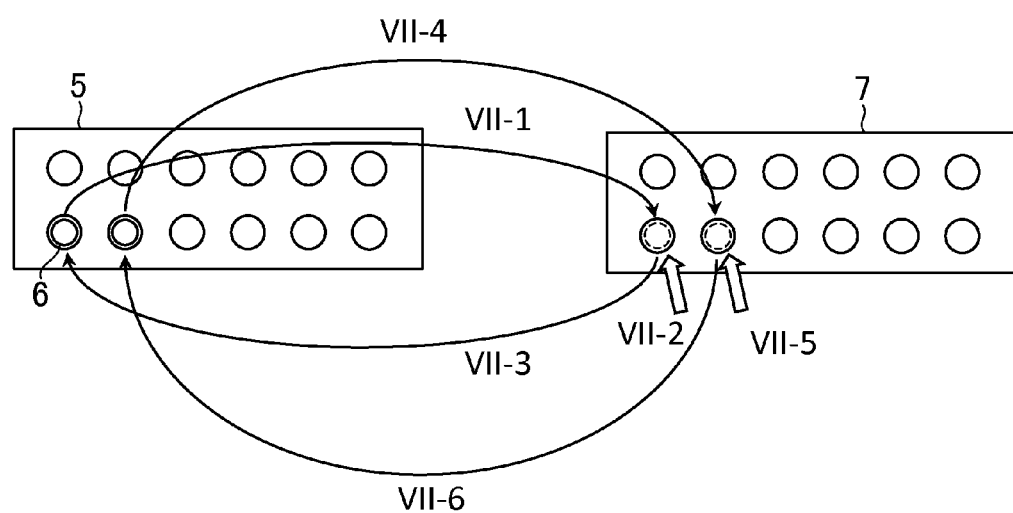
FIG. 7 is a diagram for illustrating operations of the robot in jobs generated based on the second example of the protocol chart.

FIG. 6 is a diagram for illustrating a second example of the protocol chart acquired by the operation command generation device 1 according to an embodiment of the present invention. Further, FIG. 7 is a diagram for illustrating operations of the robot 3 in jobs generated based on the second example of the protocol chart.

In the second example, the initial symbol 100 in which "Tube 1" is written, the final symbol 101, and the procedure line 102 connecting the initial symbol 100 and the final symbol 101, and the initial symbol 100 in which "Tube 2" is written, the final symbol 101, and the procedure line 102 connecting the initial symbol 100 and the final symbol 101, are arranged at positions offset from each other in the second direction. The protocol according to the second example shows that Process A is carried out on a "Tube 1" (first microtube) based on Condition A, a Process B is carried out on a "Tube 2" (second microtube) based on a Condition B, and each of those microtubes is stored in a 4° C. thermostatic bath. In this case, the process symbol 103 representing Process A to be carried out on the first microtube is arranged further toward the initial symbol 100 side (upper side of the drawing sheet) than the process symbol 103 representing Process B to be carried out on the second microtube. This arrangement relationship indicates the order in which the processes are to be executed. In other words, the second example of the protocol chart shows that Process A is carried out on the first microtube, and then Process B is carried out on the second microtube. In the protocol chart illustrated in this example, it is understood that containers represented by different initial symbols 100 are different containers containing different process subjects from each other. In this case, from the perspective of preventing contamination, and the perspective of facilitating tracking of a container when a person is observing, it is desired to transfer the container for which a process has finished to the subrack 5 after the process carried out on the container has finished but before a container containing a different process subject is arranged in the main rack 7.

The same-container determination unit 16 according to this embodiment is configured to determine whether or not a plurality of process symbols 103 represent processes to be carried out on the same container. In this example, the plurality of process symbols 103 (the process symbol 103 representing Process A and the process symbol 103 representing Process B) represent processes to be carried out on different containers (the first microtube and the second microtube). Therefore, the same-container determination unit 16 determines that the plurality of process symbols 103 do not represent processes to be carried out on the same container.

The arrangement job generation unit 13 is configured to generate, when it is determined by the same-container determination unit 16 that the plurality of process symbols 103 do not represent processes to be carried out on the same container, for each container, a job for causing the process system 200 to arrange the container from the subrack 5, which is the retreat area, in the main rack 7, which is the work area. Specifically, the arrangement job generation unit 13 generates a job for causing the robot 3 to arrange the first microtube in the main rack 7, and a job for causing the robot 3 to arrange the second microtube in the main rack 7 after Process A has been carried out on the first microtube and the first microtube has been transferred to the subrack 5.

The process job generation unit 14 is configured to generate, when it is determined by the same-container determination unit 16 that the plurality of process symbols 103 do not represent processes to be carried out on the same container, for each container, based on the process symbol 103, a job for causing the process system 200 to carry out the process on the container. Specifically, the process job generation unit 14 generates a job for causing the robot 3 to carry out Process A on the first microtube at the main rack 7, and a job for causing the robot 3 to carry out Process B on the second microtube at the main rack 7 after the first microtube has been transferred to the subrack 5.

The transfer job generation unit 15 is configured to generate, when it is determined by the same-container determination unit 16 that the plurality of process symbols 103 do not represent processes to be carried out on the same container, for each container, a job for causing the process system 200 to transfer the container from the main rack 7, which is the work area, to the subrack 5, which is the retreat area, after the process represented by the process symbol has been carried out. Specifically, the transfer job generation unit 15 generates a job for transferring the first microtube to the subrack 5 after Process A has been carried out on the first microtube, and a job for causing the second microtube to retreat to the subrack 5 after Process B has been carried out on the second microtube.

As illustrated in FIG. 7, first, the first microtube is arranged in the storage area at the lower left of the subrack 5, and the second microtube is arranged in the second storage area from the left on the lower side of the subrack 5. The robot 3 is operated based on the job generated by the arrangement job generation unit 13 so that the first microtube is arranged in the storage area at the lower left of the main rack 7 from the storage area at the lower left of the subrack 5 (arrow VII-1). Further, the robot 3 is operated based on the job generated by the process job generation unit 14 so that Process A is carried out on the first microtube (arrow VII-2). In addition, the robot 3 is operated based on the job generated by the transfer job generation unit 15 so that the first microtube is transferred to the storage area at the lower left of the subrack 5 (arrow VII-3). At this stage, the main rack 7 returns to a state in which no containers are stored in the main rack 7. Then, the robot 3 is operated based on the job generated by the arrangement job generation unit 13 so that the second microtube is arranged in the second storage area from the left on the lower side of the main rack 7 from the second storage area from the left on the lower side of the subrack 5 (arrow VII-4). Further, the robot 3 is operated based on the job generated by the process job generation unit 14 so that Process A is carried out on the second microtube (arrow VII-5). In addition, the robot 3 is operated based on the job generated by the transfer job generation unit 15 so that the second microtube is transferred to the second storage area from the left on the lower side of the subrack 5 (arrow VII-6).

Thus, the operation command generation device 1 according to this embodiment is configured to generate, when the plurality of process symbols represent processes to be carried out on different containers, for each container, a job for arranging the container in the work area, a job for carrying out the process on the container, and a job for transferring the container to the retreat area. The operation command generation device 1 according to this embodiment is configured to generate, after the process on the container has finished, but before a container containing a different process subject is arranged in the main rack 7, a job for transferring the container for which the process has finished to the subrack 5. Therefore, a job is automatically generated that prevents contamination and facilitates tracking of the container when a person is observing.

Figure 8:
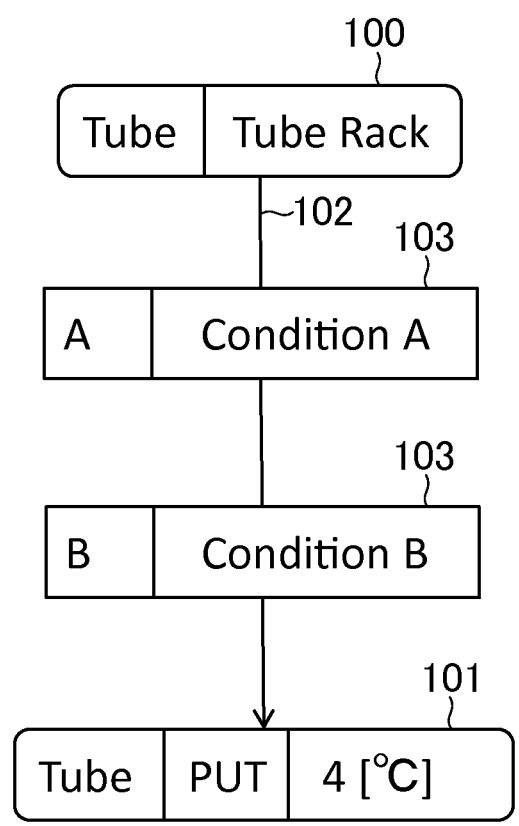
FIG. 8 is a diagram for illustrating a third example of the protocol chart acquired by the operation command generation device according to the embodiment of the present invention.
Figure 9:
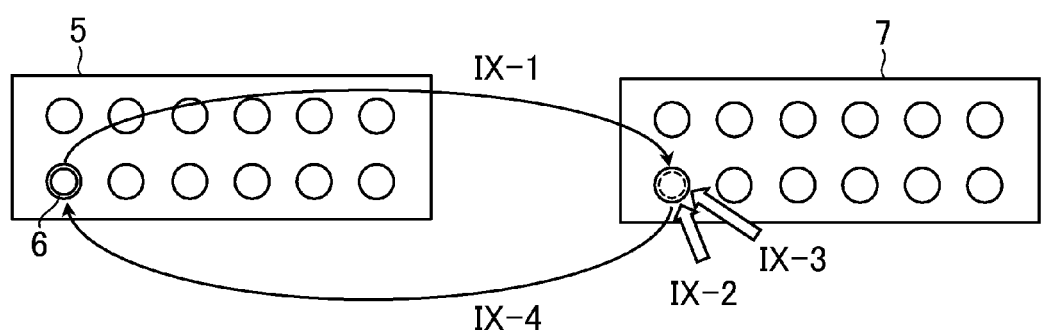
FIG. 9 is a diagram for illustrating operations of the robot in jobs generated based on the third example of the protocol chart.

FIG. 8 is a diagram for illustrating a third example of the protocol chart acquired by the operation command generation device 1 according to this embodiment. Further, FIG. 9 is a diagram for illustrating operations of the robot 3 in jobs generated based on the third example of the protocol chart. The protocol according to the third example shows that Process A is carried out on a microtube based on Condition A, Process B is then carried out based on Condition B, and the microtube is stored in a 4° C. thermostatic bath. The protocol according to this example shows that processes are consecutively carried out on the same container. With the operation command generation device 1 according to this embodiment, when processes are consecutively carried out in this manner on the same container, the work time can be shortened while preventing different process subjects from mixing. Such a case is now described below in more detail.

The same-container determination unit 16 according to this embodiment is configured to determine whether or not a plurality of process symbols 103 represent processes to be carried out on the same container. In this example, the plurality of process symbols 103 (the process symbol 103 representing Process A and the process symbol 103 representing Process B) represent processes to be carried out on the same container (single microtube). Therefore, the same-container determination unit 16 determines that the plurality of process symbols 103 represent processes to be carried out on the same container.

The arrangement job generation unit 13 is configured to generate, when it is determined by the same-container determination unit 16 that the plurality of process symbols 103 represent processes to be carried out on the same container, at least one job for causing the process system 200 to arrange the container from the subrack 5, which is the retreat area, in the main rack 7, which is the work area.

Specifically, the arrangement job generation unit 13 generates one job for arranging, by the robot 3, the microtube 6 in the main rack 7.

The process job generation unit 14 is configured to generate, when it is determined by the same-container determination unit 16 that the plurality of process symbols 103 represent processes to be carried out on the same container, based on the plurality of process symbols 103, jobs for causing the process system 200 to consecutively carry out the processes represented by the plurality of process symbols 103 on the container. Specifically, the process job generation unit 14 generates jobs for consecutively carrying out, by the robot 3, Process A and Process B on the first microtube 6 at the main rack 7.

The transfer job generation unit 15 is configured to generate, when it is determined by the same-container determination unit 16 that the plurality of process symbols 103 represent processes to be carried out on the same container, a job for causing the process system 200 to transfer the container from the main rack 7, which is the work area, to the subrack 5, which is the retreat area, at least after a final process among the processes represented by the plurality of process symbols 103 has been carried out. Specifically, the transfer job generation unit 15 generates a job for transferring, by the robot 3, the microtube 6 to the subrack 5 after Process B, which is the final process, has been carried out.

As illustrated in FIG. 9, first, the microtube 6 is arranged in the storage area at the lower left of the subrack 5. The robot 3 is operated based on the job generated by the arrangement job generation unit 13 so that the microtube 6 is moved from the storage area at the lower left of the subrack 5 and arranged in the storage area at the lower left of the main rack 7 (arrow IX-1). Further, the robot 3 is operated based on the jobs generated by the process job generation unit 14 so that Process A and Process B are consecutively carried out on the microtube 6 (arrow IX-2 and arrow IX-3). In addition, the robot 3 is operated based on the job generated by the transfer job generation unit 15 so that the microtube 6 is transferred to the storage area at the lower left of the subrack 5 (arrow IX-4).

Thus, the operation command generation device 1 according to this embodiment is configured to generate, when a plurality of process symbols represent processes to be carried out on the same container, a job for consecutively carrying out the processes without returning the container to the retreat area for each process. Therefore, an unnecessary operation of returning the container to the retreat area after each process despite the fact that the processes are carried out on the same container can be prevented, and hence a job for realizing an efficient operation is automatically generated.

Figure 10:
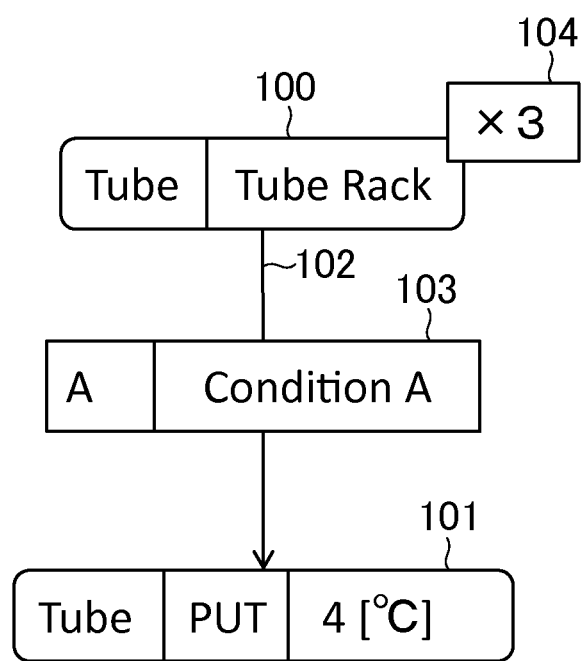
FIG. 10 is a diagram for illustrating a fourth example of the protocol chart acquired by the operation command generation device according to the embodiment of the present invention.
Figure 11:
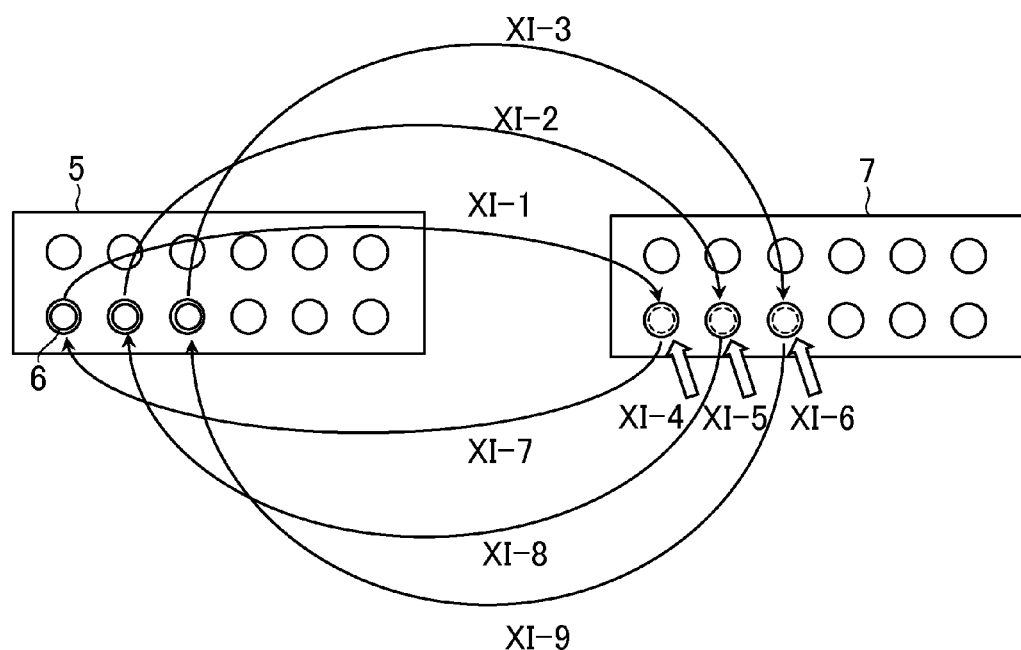
FIG. 11 is a diagram for illustrating operations of the robot in jobs generated based on the fourth example of the protocol chart.

FIG. 10 is a diagram for illustrating a fourth example of the protocol chart acquired by the operation command generation device 1 according to this embodiment. In FIG. 10, a number-of-containers symbol 104 is arranged on top of the initial symbol 100. The number-of-containers symbol 104 is associated with the process symbol 103 connected to the initial symbol 100 by the procedure line 102 by arranging the number-of-containers symbol 104 on top of the initial symbol 100. The number-of-containers symbol 104 represents with the characters "×3" that the process represented by the process symbol 103 is to be repeated three times on the same type of container. Further, FIG. 11 is a diagram for illustrating operations of the robot 3 in jobs generated based on the fourth example of the protocol chart. The protocol according to the fourth example shows that Process A is carried out on the first microtube to the third microtube based on Condition A, and the three microtubes are stored in a 4° C. thermostatic bath. In this case, the three containers represented by the initial symbol 100 and the number-of-containers symbol 104 can be understood as containing the same or the same type of process subject. Further, the process to be carried out on each of the three containers is also the same. Therefore, it can be considered that the risk of different process subjects being mixed is low even if the three containers are simultaneously arranged in the work area and the process is carried out.

The number-of-containers extraction unit 17 according to this embodiment is configured to extract the number of containers associated with the process symbol 103. In this example, the number of containers is three. Further, the arrangement setting unit 18 according to this embodiment is configured to set an arrangement of the containers in the work area for the number of containers extracted by the number-of-containers extraction unit 17 so that the containers are not duplicately arranged in the same storage area. In this example, the arrangement setting unit 18 sets an arrangement for three microtubes in the main rack 7, which is the work area, so that the containers are not duplicately arranged in the same storage area. Specifically, the arrangement setting unit 18 sets the arrangement so as to arrange the first microtube in the storage area at the lower left of the main rack 7, the second microtube in the second storage area from the left on the lower side of the main rack 7, and the third microtube in the third storage area from the left on the lower side of the main rack 7.

The arrangement job generation unit 13 is configured to generate, based on the setting of the arrangement setting unit 18, a job for causing the process system 200 to move the container from the subrack 5, which is the retreat area, and arrange the container in the main rack 7, which is the work area, for each of the number of containers extracted by the number-of-containers extraction unit 17. Specifically, the arrangement job generation unit 13 generates three jobs for arranging, by the robot 3, the first microtube to the third microtube in the first storage area to the third storage area from the left on the lower side of the main rack 7, respectively.

The process job generation unit 14 is configured to generate, based on the process symbol 103, for each of the number of containers extracted by the number-of-containers extraction unit 17, a job for causing the process system 200 to repeat the process to be carried out on the container. Specifically, the process job generation unit 14 generates three jobs for repeating, by the robot 3, Process A at the main rack 7 on each of the first microtube to the third microtube.

The transfer job generation unit 15 is configured to generate, for each of the number of containers extracted by the number-of-containers extraction unit 17, a job for causing the process system 200 to transfer the container from the main rack 7, which is the work area, to the subrack 5, which is the retreat area. Specifically, the transfer job generation unit 15 generates three jobs for transferring, by the robot 3, the first microtube to the third microtube to the first storage area to the third storage area from the left on the lower side of the subrack 5, respectively.

As illustrated in FIG. 11, first, the first microtube to the third microtube are arranged in the first storage area to the third storage area from the left on the lower side of the subrack 5, respectively. The robot 3 is operated based on the jobs generated by the arrangement job generation unit 13 so that the first microtube to the third microtube are moved from the first storage area to the third storage area from the left on the lower side of the subrack 5 and arranged in the first storage area to the third storage area from the left on the lower side of the main rack 7, respectively (arrow XI-1, arrow XI-2, and arrow XI-3). Further, the robot 3 is operated based on the jobs generated by the process job generation unit 14 so that Process A is repeatedly carried out on the first microtube to the third microtube (arrow XI-4, arrow XI-5, and arrow XI-6). In addition, the robot 3 is operated based on the jobs generated by the transfer job generation unit 15 so that the first microtube to the third microtube are transferred to the first storage area to the third storage area from the left on the lower side of the subrack 5, respectively (arrow XI-7, arrow XI-8, and arrow XI-9).

Thus, the operation command generation device 1 according to this embodiment is configured to generate, when the process symbol represents a process to be carried out on a plurality of containers, a job for consecutively carrying out the processes without returning the container to the retreat area for each process. Therefore, an unnecessary operation of returning the container to the retreat area after each process despite the fact that the same process is repeatedly carried out on a plurality of the same type of containers can be prevented, and a job for realizing an efficient operation is automatically generated.

Figure 12:
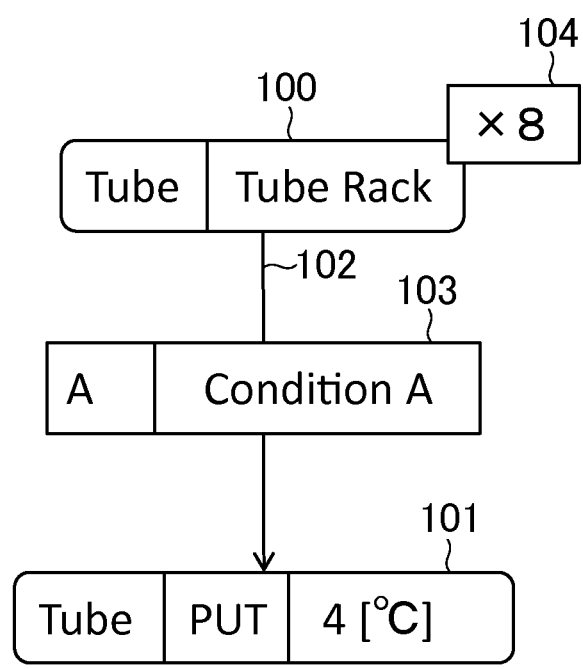
FIG. 12 is a diagram for illustrating a fifth example of the protocol chart acquired by the operation command generation device according to the embodiment of the present invention.
Figure 13A:
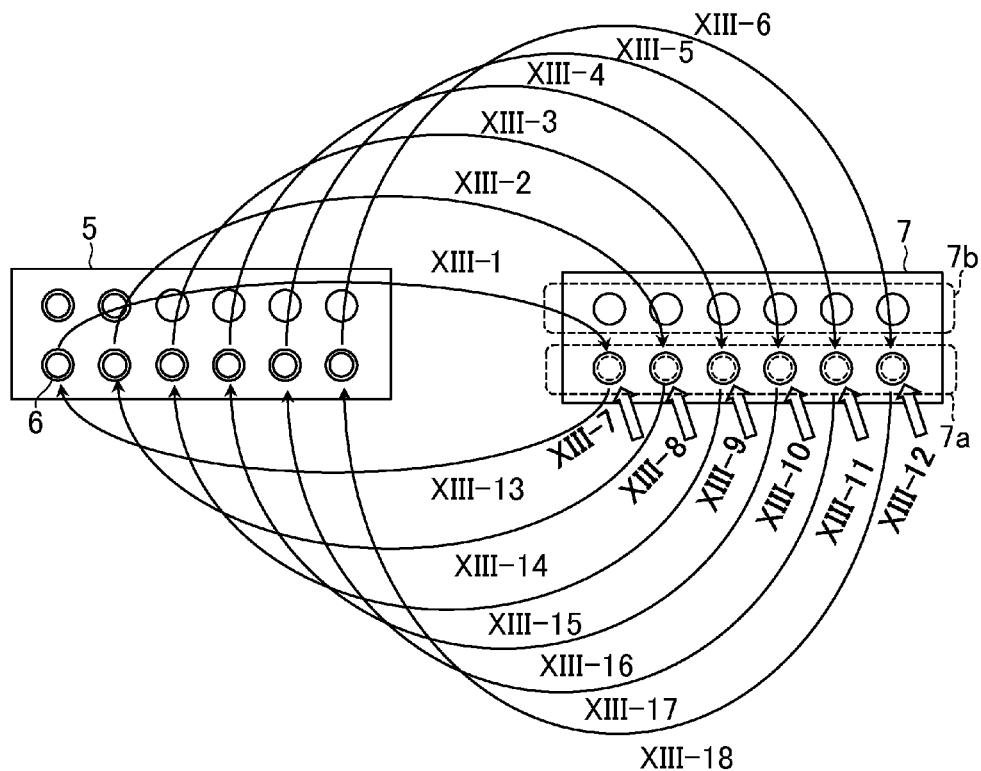
FIG. 13A is a diagram for illustrating a first part of the operations of the robot in jobs generated based on the fifth example of the protocol chart.
Figure 13B:
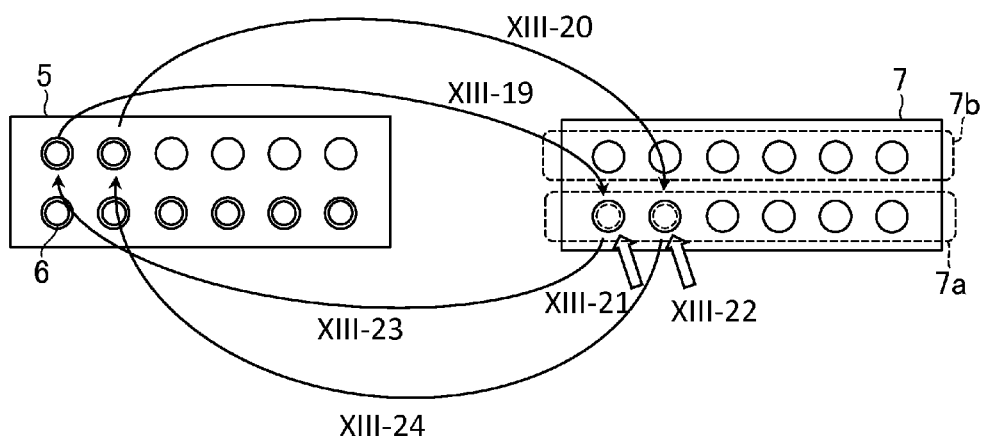
FIG. 13B is a diagram for illustrating a second part of the operations of the robot in the jobs generated based on the fifth example of the protocol chart.

FIG. 12 is a diagram for illustrating a fifth example of the protocol chart acquired by the operation command generation device 1 according to this embodiment. In FIG. 12, the number-of-containers symbol 104 is arranged on top of the initial symbol 100. The number-of-containers symbol 104 is associated with the process symbol 103 connected to the initial symbol 100 by the procedure line 102 by arranging the number-of-containers symbol 104 on top of the initial symbol 100. The number-of-containers symbol 104 represents with the characters "×8" that the process represented by the process symbol 103 is to be repeated eight times on the same type of container. Further, FIG. 13A is a diagram for illustrating a first part of the operations of the robot 3 in jobs generated based on the fifth example of the protocol chart. FIG. 13B is a diagram for illustrating a second part of the operations of the robot 3 in jobs generated based on the fifth example of the protocol chart. The protocol according to the fifth example shows that Process A is carried out on the first microtube to the eighth microtube based on Condition A, and the eight microtubes are stored in a 4° C. thermostatic bath. In this case, in order to enable the user to easily determine whether the robot 3 is carrying out the process on a container itself or whether the robot 3 is carrying out a transfer process for transferring the process subject contained in the container to another container, it is desired that for processes to be carried out on a container, the container be arranged in the row on a near side (row on the robot 3 side, that is, the bottom row as shown in the drawing sheet; hereinafter referred to as "first row 7a"), which is the first range of the main rack 7, and that when carrying out a transfer process, the row on the far side (row on the opposite side to the robot 3, that is, the top row as shown in the drawing sheet; hereinafter referred to as "second row 7b"), which is the second range of the main rack 7, be used. Therefore, by using the rows of the main rack 7 differently, a transfer process can be clearly distinguished from a non-transfer process, which allows a transfer process and a non-transfer process to be clearly distinguished from each other when a person is observing how the robot 3 is executing the protocol.

The number-of-containers extraction unit 17 according to this embodiment is configured to extract the number of containers associated with the process symbol 103. In this example, the number of containers is eight. Further, the arrangement possibility determination unit 19 according to this embodiment is configured to determine whether or not all of the number of containers extracted by the number-of-containers extraction unit 17 can be arranged in the first row 7a of the main rack 7. In this example, the first row 7a of the main rack 7 has six storage areas. Therefore, the arrangement possibility determination unit 19 determines that not all of the eight containers can be arranged in the first row 7a of the main rack 7.

The arrangement job division unit 13a is configured to divide, when it is determined by the arrangement possibility determination unit 19 that not all of the containers can be arranged in the first row 7a of the main rack 7, the job for causing the process system 200 to arrange the containers into two or more jobs for arranging in the first row 7a the number of containers that can be arranged in the first row 7a. Specifically, the arrangement job division unit 13a divides the job for arranging the first container to the eighth container in the main rack 7 into six jobs for arranging the first microtube to the sixth microtube in the first storage area to the sixth storage area from the left in the first row 7a of the main rack 7, respectively, and two jobs for arranging the seventh microtube and the eighth microtube in the first storage area and the second storage area from the left in the first row 7a of the main rack 7, respectively.

The process job division unit 14a is configured to divide, when it is determined by the arrangement possibility determination unit 19 that not all of the containers can be arranged in the first row 7a of the main rack 7, based on the process symbol 103, the job for causing the process system 200 to carry out the process represented by the process symbol 103 into two or more jobs to be carried out on each of the number of containers that can be arranged in the first row 7a. Specifically, the process job division unit 14a divides the job for carrying out Process A on the first microtube to the eighth microtube into six jobs for repeating Process A on each of the first microtube to the sixth microtube at the main rack 7, and two jobs for repeating Process A on each of the seventh microtube and the eighth microtube at the main rack 7.

The transfer job division unit 15a is configured to divide, when it is determined by the arrangement possibility determination unit 19 that not all of the containers can be arranged in the first row 7a of the main rack 7, the job for causing the process system 200 to retreat the container into two or more jobs based on the division carried out by the process job division unit 14a. Specifically, the transfer job division unit 15a divides, in the same manner as the process job division unit 14a, the job for transferring the first microtube to the eighth microtube to the subrack 5 into six jobs for transferring the first microtube to the sixth microtube to the first storage area to the sixth storage area from the left on the lower side of the subrack 5, respectively, and two jobs for transferring the seventh microtube and the eighth microtube to the first storage area and the second storage area from the left on the upper side of the subrack 5, respectively.

Note that, it is not always necessary for the arrangement job division unit 13a, the process job division unit 14a, and the transfer job division unit 15a to divide the job so that all of the storage areas of the first row 7a of the main rack 7 are used. In other words, as another example of the above-mentioned example, the jobs for arranging, processing, and transferring the first microtube to the eighth microtube may be divided into jobs for arranging, processing, and transferring the first microtube to the fourth microtube and jobs for arranging, processing, and transferring the fifth microtube to the eighth microtube. However, it is necessary for the arrangement job division unit 13a, the process job division unit 14a, and the transfer job division unit 15a to divide the jobs into the same number of jobs.

As illustrated in FIG. 13A, first, the first microtube to the sixth microtube are arranged in the first storage area to the sixth storage area from the left on the lower side of the subrack 5, respectively. Further, the seventh microtube and the eighth microtube are arranged in the first storage area and the second storage area from the left on the upper side of the subrack 5, respectively. The robot 3 is operated based on the jobs divided by the arrangement job division unit 13a so that the first microtube to the sixth microtube are moved from the first storage area to the sixth storage area from the left on the lower side of the subrack 5, and arranged at the first storage area to the sixth storage area from the left in the first row 7a of the main rack 7, respectively (arrow XIII-1, arrow XIII-2, arrow XIII-3, arrow XIII-4, arrow XIII-5, and arrow XIII-6). Further, the robot 3 is operated based on the jobs divided by the process job division unit 14a so that Process A is repeatedly carried out on the first microtube to the sixth microtube (arrow XIII-7, arrow XIII-8, arrow XIII-9, arrow XIII-10, arrow XIII-11, and arrow XIII-12). In addition, the robot 3 is operated based on the jobs divided by the transfer job division unit 15a so that the first microtube to the sixth microtube are transferred to the first storage area to the sixth storage area from the left on the lower side of the subrack 5, respectively (arrow XIII-13, arrow XIII-14, arrow XIII-15, arrow XIII-16, arrow XIII-17, and arrow XIII-18).

As illustrated in FIG. 13B, the robot 3 is operated based on the jobs divided by the arrangement job division unit 13a so that the seventh microtube and the eighth microtube are moved from the first storage area and the second storage area from the left on the upper side of the subrack 5, and arranged at the first storage area and the second storage area from the left in the first row 7a of the main rack 7, respectively (arrow XIII-19 and arrow XIII-20). Further, the robot 3 is operated based on the jobs divided by the process job division unit 14a so that Process A is repeatedly carried out on the seventh microtube and the eighth microtube (arrow XIII-21 and arrow XIII-22). In addition, the robot 3 is operated based on the jobs divided by the transfer job division unit 15a so that the seventh microtube and the eighth microtube are transferred to the first storage area and the second storage area from the left on the upper side of the subrack 5, respectively (arrow XIII-23 and arrow XIII-24).

Thus, the operation command generation device 1 according to this embodiment is configured to divide, when not all of the containers can be arranged in the first row 7a of the main rack 7, the job for arranging the containers in the first row 7a of the main rack 7, the job for carrying out the process on the container, and the job for transferring the containers to the subrack 5, into jobs that allow all of the containers to be arranged in the first row 7a. As a result, efficient jobs are generated when repeating the same process on a plurality of containers, while clarifying the difference with the transfer process described later by arranging the containers in the first row 7a of the main rack 7 and carrying out the process on the containers.

The operation command generation device 1 according to this embodiment is capable of generating, based on the fifth example of the protocol chart shown in FIG. 12, jobs different from the jobs illustrated in FIG. 13A and FIG. 13B. The number-of-containers extraction unit 17 according to this embodiment is configured to extract the number of containers associated with the process symbol 103. In this example, as already described above, the number of containers is eight. Further, the arrangement possibility determination unit 19 according to this embodiment is configured to determine whether or not all of the number of containers extracted by the number-of-containers extraction unit 17 can be arranged in the first row 7a of the main rack 7. In this example, the first row 7a of the main rack 7 has six storage areas. Therefore, the arrangement possibility determination unit 19 determines that not all of the eight containers can be arranged in the first row 7a of the main rack 7.

The arrangement job generation unit 13 is configured to generate, when it is determined by the arrangement possibility determination unit 19 that not all of the containers can be arranged in the first row 7a of the main rack 7, a job for causing the process system 200 to arrange at least the containers that cannot be arranged in the first row 7a in the second row 7b of the main rack 7 from the subrack 5, which is the retreat area. Specifically, the arrangement job generation unit 13 generates six jobs for arranging, by the robot 3, the first microtube to the sixth microtube in the first storage area to the sixth storage area from the left in the first row 7a of the main rack 7, respectively, and two jobs for arranging, by the robot 3, the seventh microtube and the eighth microtube in the first storage area and the second storage area from the left in the second row 7b of the main rack 7, respectively.

The process job generation unit 14 is configured to generate, based on the process symbol 103, jobs for causing the process system 200 to carry out the process on the containers in the first row 7a and second row 7b of the main rack 7. Specifically, the process job generation unit 14 generates eight jobs for repeating, by the robot 3, Process A on each of the first microtube to the eighth microtube at the main rack 7.

The transfer job generation unit 15 is configured to generate jobs for causing the process system 200 to transfer the containers from the first row 7a and second row 7b of the main rack 7 to the subrack 5, which is the retreat area, after the process represented by the process symbol 103 has been carried out. Specifically, the transfer job generation unit 15 generates six jobs for transferring, by the robot 3, the first microtube to the sixth microtube to the first storage area to the sixth storage area from the left on the lower side of the subrack 5, respectively, and two jobs for transferring, by the robot 3, the seventh microtube and the eighth microtube to the first storage area and the second storage area from the left on the upper side of the subrack 5, respectively.

Thus, the operation command generation device 1 according to this embodiment is capable of generating, when not all of the containers can be arranged in the first row 7a of the main rack 7, a job using the storage areas of the second row 7b of the main rack 7. The user of the operation command generation device 1 according to this embodiment can improve operational efficiency, such as a shortened work time, by selecting to generate a job that uses the storage areas of the second row 7b of the main rack 7.

Figure 14:
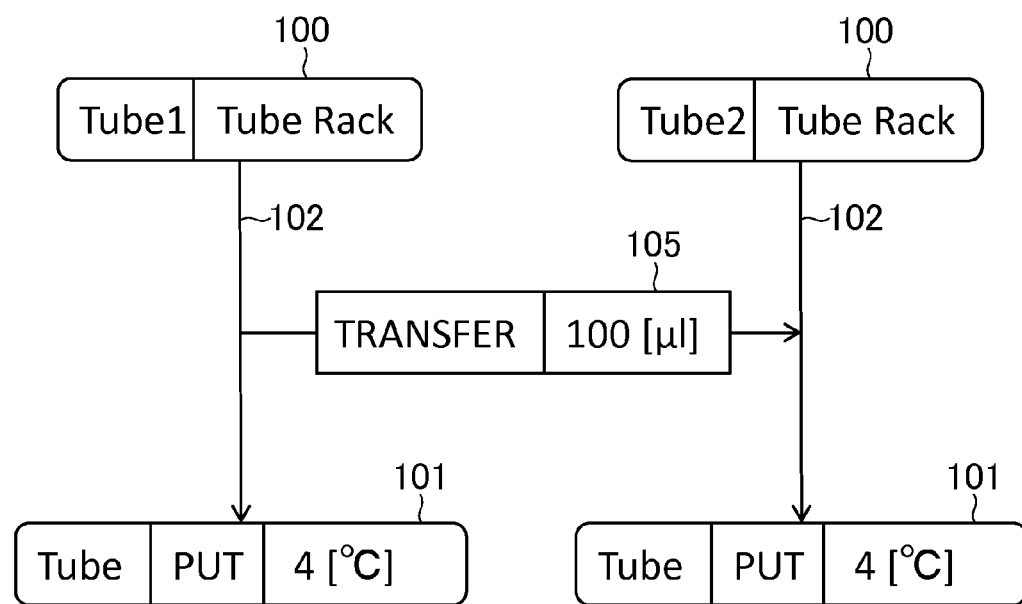
FIG. 14 is a diagram for illustrating a sixth example of the protocol chart acquired by the operation command generation device according to the embodiment of the present invention.
Figure 15:
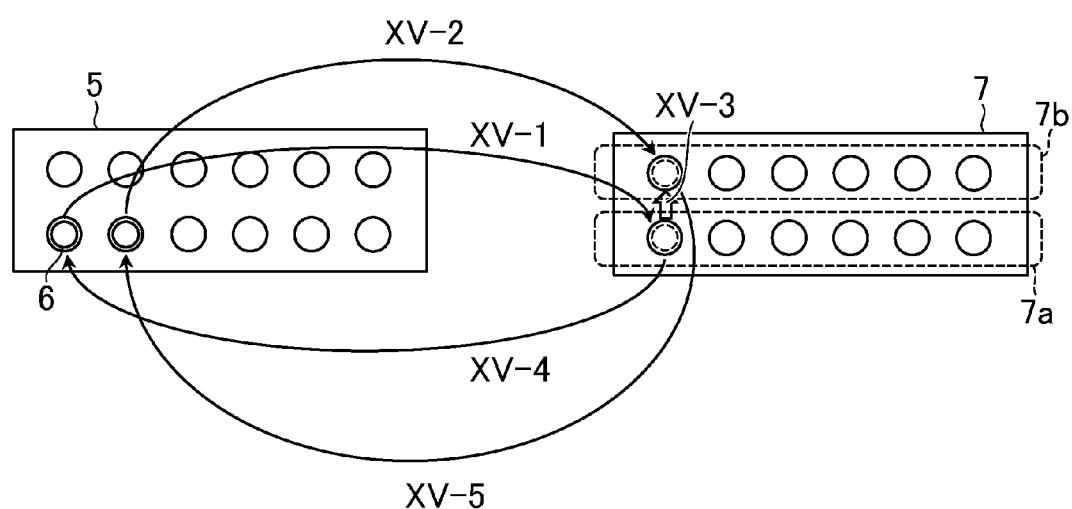
FIG. 15 is a diagram for illustrating operations of the robot in jobs generated based on the sixth example of the protocol chart.

FIG. 14 is a diagram for illustrating a sixth example of the protocol chart acquired by the operation command generation device 1 according to an embodiment of the present invention. Further, FIG. 15 is a diagram for illustrating operations of the robot 3 in jobs generated based on the sixth example of the protocol chart. In the protocol chart according to the sixth example, a transfer symbol 105 is arranged from the procedure line 102 connected to the initial symbol 100 of "Tube 1" toward the procedure line 102 connected to the initial symbol 100 of "Tube 2". The transfer symbol 105 represents a process for transferring a designated amount of a process subject contained in a container. The protocol according to the sixth example shows that 100 μl of the process subject contained in "Tube 1" (first microtube) is transferred to "Tube 2" (second microtube), and that both microtubes are stored in a 4° C. thermostatic bath.

In carrying out the transfer process, the process subject is transferred by arranging a transfer source container in a transfer source range (in this example, the first row 7a) of the main rack 7, and arranging a transfer destination container in a transfer destination range (in this example, the second row 7b) of the main rack 7, which is a position corresponding to the transfer source container. Arranging the transfer source containers and the transfer destination containers so as to correspond to each other on a one-to-one basis allows suppression of an error in which the person confirming the operations of the robot 3 makes a mistake regarding the transfer source containers and the transfer destination containers. In this example, for ease of description, an example is illustrated in which the process subject is transferred from one container to one container. However, the number of transfer source containers and the number of transfer destination containers may be two or more. Further, the number of transfer source containers and the number of transfer destination containers do not need to match. When the number of transfer source containers and the number of transfer destination containers do not match, the transfer source containers and the transfer destination containers may be arranged so as to correspond to each other on a many-to-one basis, a one-to-many basis, or a many-to-many basis. Even in such a case, the transfer source containers are arranged in the first row 7a of the main rack 7, and the transfer destination containers are arranged in the second row 7b of the main rack 7. Note that, in this example, the first range of the main rack 7 and the transfer source range are the same range, and the second range of the main rack 7 and the transfer destination range are the same range. However, the first range of the main rack 7 and the transfer source range do not need to match, and the second range of the main rack 7 and the transfer destination range do not need to match. Normally, those ranges are set to match each other, and hence setting those ranges so as to match each other facilitates understanding of the protocol when a person is observing the operations of the robot 3.

The container arrangement job generation unit 20 is configured to generate jobs for causing the process system 200 to arrange the first container containing the process subject in the first row 7a of the main rack 7, which is the transfer source range, and the second container in the second row 7b of the main rack 7, which is the transfer destination range. Specifically, the container arrangement job generation unit 20 generates a job for arranging, by the robot 3, the first microtube in the storage area at the leftmost side in the first row 7a of the main rack 7, and a job for arranging, by the robot 3, the second microtube in the storage area at the leftmost side in the second row 7b of the main rack 7.

The process subject transfer job generation unit 21 is configured to generate, based on the transfer symbol 105 contained in the protocol chart, a job for causing the process system 200 to transfer the process subject from the first microtube, which is the first container, to the second microtube, which is the second container. Specifically, the process subject transfer job generation unit 21 generates a job for sucking up, by the robot 3, 100 μl of the process subject contained in the first microtube into the pipette 4, and transferring the sucked process subject to the second microtube.

The container transfer job generation unit 22 is configured to generate a job, which is to be carried out after the transfer of the process subject, for causing the process system 200 to transfer the first microtube, which is the first container, from the first row 7a of the main rack 7 to the storage area at the lower left of the subrack 5, which is the retreat area, and a job, which is to be carried out after the transfer of the process subject, for causing the process system 200 to transfer the second microtube, which is the second container, from the second row 7b of the main rack 7 to the second storage area from the left on the lower side of the subrack 5, which is the retreat area. Specifically, the container transfer job generation unit 22 generates a job for transferring, by the robot 3, the first microtube to the storage area at the lower left of the subrack 5, and a job for transferring, by the robot 3, the second microtube to the second storage area from the left on the lower side of the subrack 5.

As illustrated in FIG. 15, first, the first microtube is arranged in the storage area at the lower left of the subrack 5, and the second microtube is arranged in the second storage area from the left on the lower side of the subrack 5. The robot 3 is operated based on the jobs generated by the container arrangement job generation unit 20 so that the first microtube is moved from the storage area at the lower left of the subrack 5 and arranged in the storage area at the leftmost side in the first row 7a of the main rack 7 (arrow XV-1), and the second microtube is moved from the second storage area from the left on the lower side of the subrack 5 and arranged in the storage area at the leftmost side in the second row 7b of the main rack 7 (arrow XV-2). Further, the robot 3 is operated based on the job generated by the process subject transfer job generation unit 21 so that the process subject is transferred from the first microtube to the second microtube (arrow XV-3). In addition, the robot 3 is operated based on the jobs generated by the container transfer job generation unit 22 so that the first microtube is transferred to the storage area at the lower left of the subrack 5 (arrow XV-4), and the second microtube is transferred to the second storage area from the left on the lower side of the subrack 5 (arrow XV-5).

Thus, with the operation command generation device 1 according to this embodiment, a job for transferring the process subject from a container arranged in the first row 7a of the main rack 7 to a container arranged in the second row 7b of the main rack 7 is automatically generated. Therefore, when a person is observing the transfer process executed by the robot 3, the fact that the transfer source range and the transfer destination range correspond to each other can be easily confirmed. As a result, the protocol is easy to understand, and making a mistake regarding the container is prevented.

Figure 16:
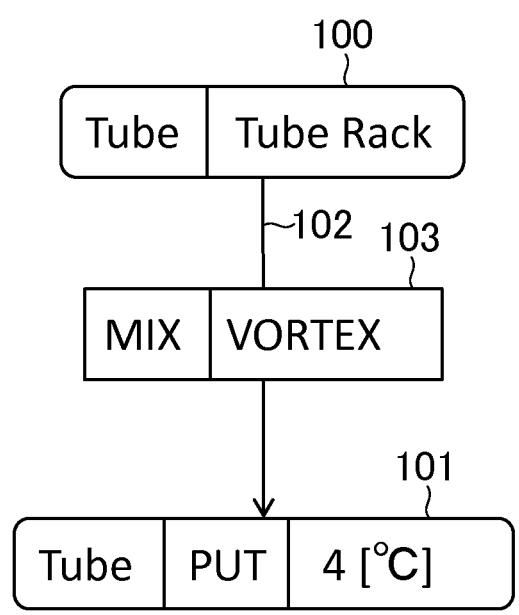
FIG. 16 is a diagram for illustrating a seventh example of the protocol chart acquired by the operation command generation device according to the embodiment of the present invention.
Figure 17:
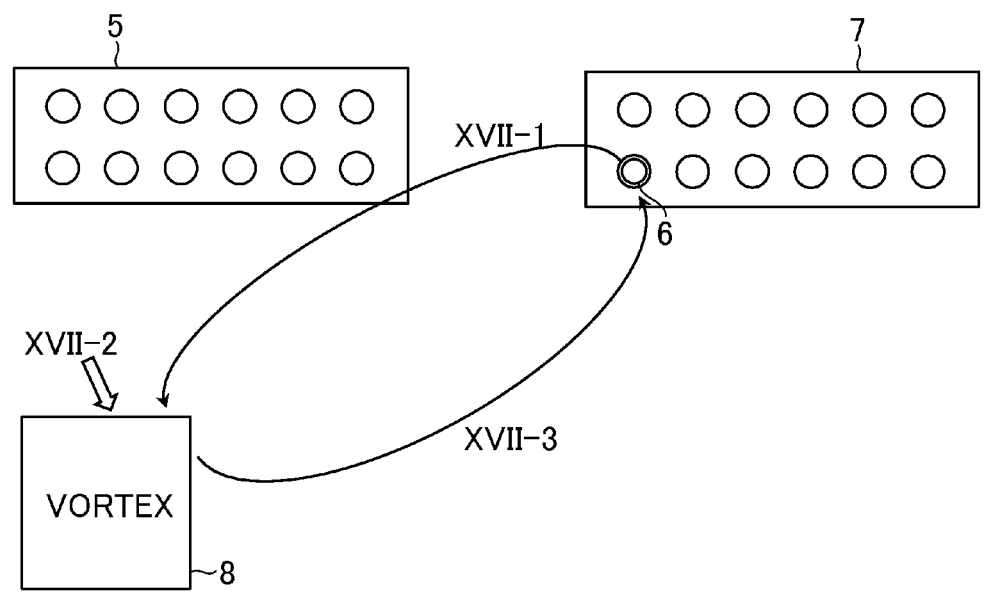
FIG. 17 is a diagram for illustrating operations of the robot in jobs generated based on the seventh example of the protocol chart.

FIG. 16 is a diagram for illustrating a seventh example of the protocol chart acquired by the operation command generation device 1 according to this embodiment. Further, FIG. 17 is a diagram for illustrating operations of the robot 3 in jobs generated based on the seventh example of the protocol chart. The protocol according to the seventh example shows that an agitation process represented as "MIX" by the process symbol 103 is carried out on a microtube by the agitator 8 represented as "VORTEX" by the process symbol 103, and that the microtube is stored in a 4° C. thermostatic bath. In this case, when carrying out a process using a peripheral device such as the agitator 8, contamination and the like are prevented by carrying out a series of operations in which the container containing the process subject is moved from the main rack 7 to the peripheral device to prepare for the process, the process using a peripheral device is carried out on the container, and after the process, the container is made to retreat from the peripheral device to the main rack 7. Further, by carrying out the process using a peripheral device on one container, the protocol is easily understood when a person observes the operations of the robot 3.

The device arrangement job generation unit 14b is configured to generate a job, which is to be carried out before the process represented by the process symbol 103, for causing the process system 200 to arrange a container from the main rack 7, which is the work area, on the agitator 8, which is a peripheral device. Specifically, the device arrangement job generation unit 14b generates a job for arranging, by the robot 3, the microtube 6 on the agitator 8 from the main rack 7, starting the agitator 8, and preparing to carry out the process with the agitator 8.

The device process job generation unit 14c is configured to generate, based on the process symbol 103, a job for causing the process system 200 to carry out the process using the agitator 8, which is a peripheral device, on the container. Specifically, the device process job generation unit 14c generates a job for carrying out, by the robot 3, the agitation process using the agitator 8 on the microtube 6. Note that, when the time for carrying out the agitation process is designated in the protocol chart, the device process job generation unit 14c generates a job for carrying out the agitation process at the designated time.

The device transfer job generation unit 14d is configured to generate, when the process represented by the process symbol is not a process to be carried out on at least the same container, a job for causing the process system 200 to transfer the container from the peripheral device to the main rack 7, which is the work area, after the process represented by the process symbol 103 has been carried out. Specifically, the device transfer job generation unit 14d generates a job for transferring, by the robot 3, the microtube 6 from the agitator 8 to the storage area in which the microtube 6 was initially stored among the storage areas of the main rack 7.

As illustrated in FIG. 17, first, the microtube 6 is arranged in the storage area at the lower left of the main rack 7. The robot 3 is operated based on the job generated by the device arrangement job generation unit 14b so that the microtube 6 is arranged on the agitator 8 from the storage area at the lower left of the main rack 7 (arrow XVII-1). Further, the robot 3 is operated based on the job generated by the device process job generation unit 14c so that the agitation process using the agitator 8 is carried out on the microtube 6 (arrow XVII-2). In addition, the robot 3 is operated based on the job generated by the device transfer job generation unit 14d so that the microtube 6 is transferred from the agitator 8 to the storage area at the lower left of the main rack 7 (arrow XVII-3).

Thus, the operation command generation device 1 according to this embodiment is configured to generate, when the process symbol represents a process using a peripheral device, a job for arranging the container in the peripheral device from the work area and carrying out the process using a peripheral device, and when a process on at least a different container is to be subsequently carried out, transferring the container to the work area. As a result, a different container is not arranged in the peripheral device, and hence contamination is prevented. Further, the operations of the robot 3 can be tracked more easily by a person, and the fact that the robot 3 is operating in a manner for preventing contamination can be easily confirmed.

Figure 18:
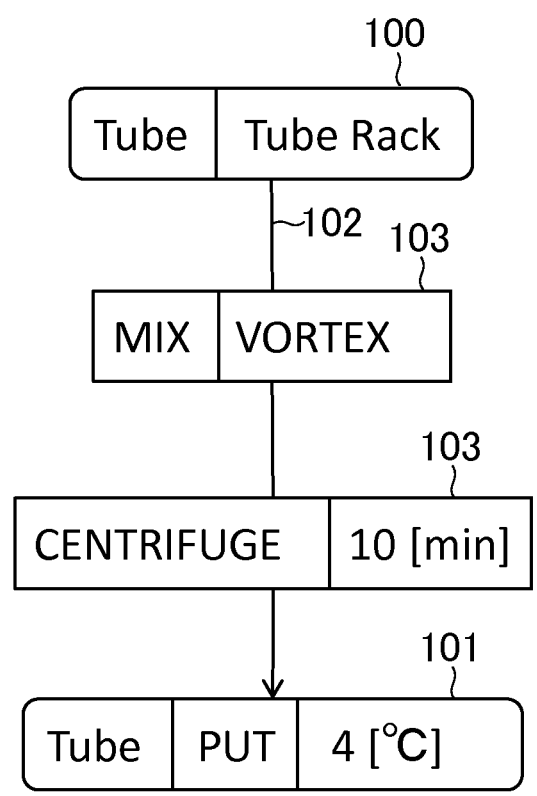
FIG. 18 is a diagram for illustrating an eighth example of the protocol chart acquired by the operation command generation device according to the embodiment of the present invention.
Figure 19:
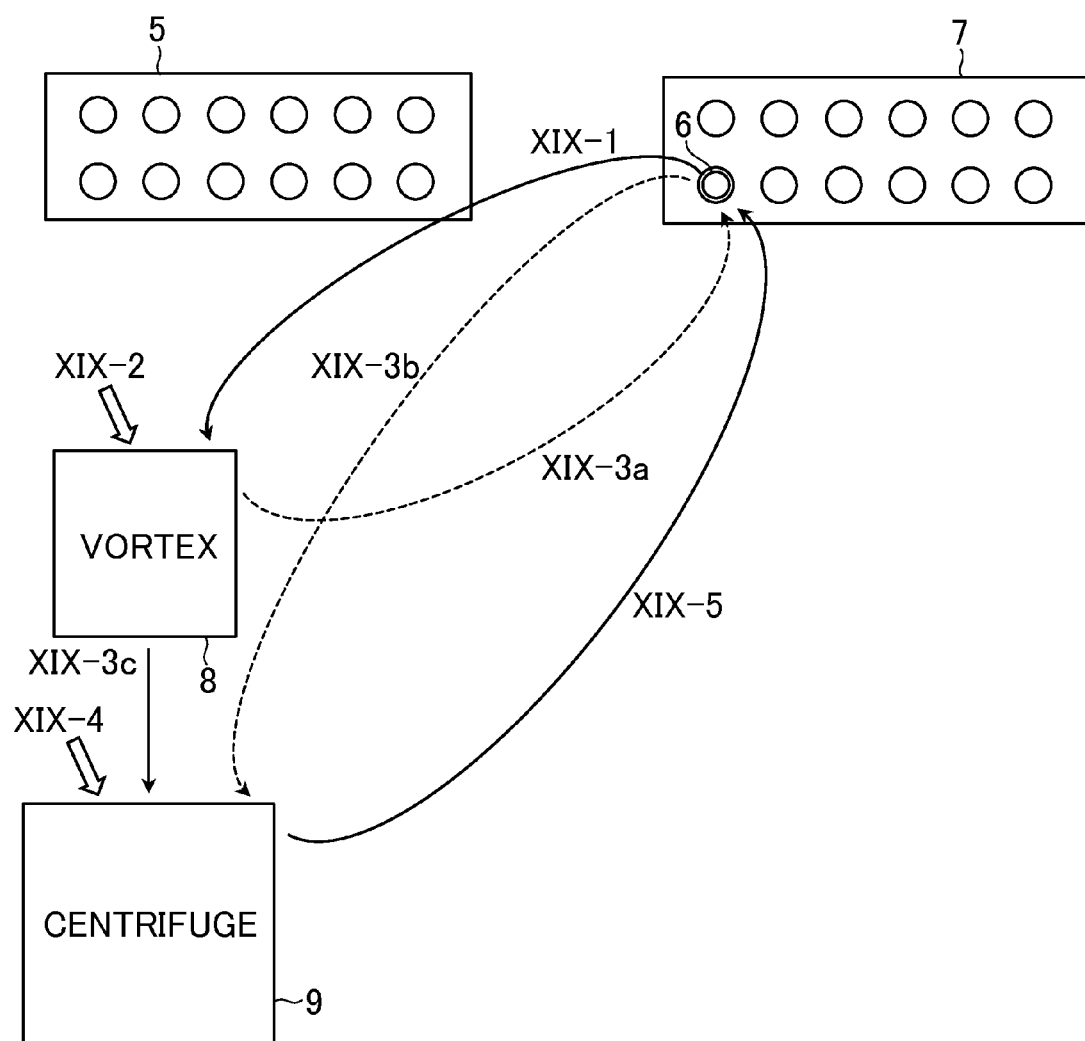
FIG. 19 is a diagram for illustrating operations of the robot in jobs generated based on the eighth example of the protocol chart.

FIG. 18 is a diagram for illustrating an eighth example of the protocol chart acquired by the operation command generation device 1 according to this embodiment. Further, FIG. 19 is a diagram for illustrating operations of the robot 3 in jobs generated based on the eighth example of the protocol chart. The protocol according to the eighth example shows that an agitation process represented as "MIX" by a first process symbol 103 is carried out on a microtube by the agitator 8 represented as "VORTEX" by the first process symbol 103, then a centrifugal separation process represented as "CENTRIFUGE" by a second process symbol 103 is carried out for 10 minutes ("10 [min]") by the centrifugal separator 9, and the microtube is stored in a 4° C. thermostatic bath. In this case, when carrying out the process using a first peripheral device and the process using a second peripheral device, the work time may be shortened by directly transferring the container from the first peripheral device to the second peripheral device.

The device arrangement job generation unit 14b is configured to generate a job, which is to be carried out before the process represented by the first process symbol 103, for causing the process system 200 to move a container from the main rack 7, which is the work area, and arrange the container on the agitator 8, which is the first peripheral device. Specifically, the device arrangement job generation unit 14b generates a job for arranging, by the robot 3, the microtube 6 on the agitator 8 from the main rack 7, starting the agitator 8, and preparing to carry out the process with the agitator 8.

The device process job generation unit 14c is configured to generate, based on the process symbol 103, a job for causing the process system 200 to carry out the process using the agitator 8, which is the first peripheral device, on the container. Specifically, the device process job generation unit 14c generates a job for carrying out, by the robot 3, the agitation process using the agitator 8 on the microtube 6. Further, the device process job generation unit 14c is configured to generate, based on the process symbol 103, a job for causing the process system 200 to carry out the process using the centrifugal separator 9, which is the second peripheral device, on the container. Specifically, the device process job generation unit 14c generates a job for carrying out, by the robot 3, the centrifugal separation process using the centrifugal separator 9 on the microtube 6.

The device-to-device transfer job generation unit 14e is configured to generate a job, which is to be carried out between the process using the agitator 8, which is a first peripheral device, and the process using the centrifugal separator 9, which is a second peripheral device, the processes being represented by a plurality of process symbols, for causing the process system 200 to transfer the container from the agitator 8, which is the first peripheral device, to the centrifugal separator 9, which is the second peripheral device. Specifically, the device-to-device transfer job generation unit 14e generates a job for transferring, by the robot 3, the container from the agitator 8 to the centrifugal separator 9 between the process using the agitator 8 and the process using the centrifugal separator 9.

The device transfer job generation unit 14d is configured to generate a job, which is to be carried out after the process represented by the second process symbol 103, for causing the process system 200 to transfer the container from the centrifugal separator 9, which is the second peripheral device, to the main rack 7, which is the work area. Specifically, the device transfer job generation unit 14d generates a job for transferring, by the robot 3, the microtube 6 from the centrifugal separator 9 to the storage area in which the microtube 6 was initially stored among the storage areas of the main rack 7.

As illustrated in FIG. 19, first, the microtube 6 is arranged in the storage area at the lower left of the main rack 7. The robot 3 is operated based on the job generated by the device arrangement job generation unit 14b so that the microtube 6 is moved from the storage area at the lower left of the main rack 7 and arranged on the agitator 8 (arrow XIX-1). Further, the robot 3 is operated based on the job generated by the device process job generation unit 14c so that the agitation process using the agitator 8 is carried out on the microtube 6 (arrow XIX-2). Then, the robot 3 is operated based on the job generated by the device-to-device transfer job generation unit 14e so that the microtube 6 is transferred from the agitator 8 to the centrifugal separator 9 (arrow XIX-3c). Further, the robot 3 is operated based on the job generated by the device process job generation unit 14c so that the centrifugal separation process using the centrifugal separator 9 is carried out on the microtube 6 (arrow XIX-4). In addition, the robot 3 is operated based on the job generated by the device transfer job generation unit 14d so that the microtube 6 is transferred from the centrifugal separator 9 to the storage area at the lower left of the main rack 7 (arrow XIX-5).

The arrow XIX-3a and the arrow XIX-3b indicated by the dotted lines each represent an operation carried out by the robot 3 when transferring the container to the main rack 7 for each of the processes using a device. In this case, after finishing the agitation process by the agitator 8 (arrow XIX-2), the robot 3 transfers the microtube 6 from the agitator 8 to the storage area at the lower left of the main rack 7 (arrow XIX-3a), and arranges the microtube 6 in the centrifugal separator 9 from the main rack 7 (arrow XIX-3b). There are no differences in the content between the process that is carried out when the container is directly transferred from the agitator 8 to the centrifugal separator 9 and the process that is carried out when the container is caused to temporarily retreat to the main rack 7. However, the work time is shorter when the container is directly transferred. The user of the operation command generation device 1 may select whether to give priority to the work time or carry out the operations as normal, that is, return the container to the main rack 7 each time a process using a peripheral device is carried out.

Thus, the operation command generation device 1 according to this embodiment is capable of generating, when a plurality of process symbols represent a process using a first peripheral device and a process using a second peripheral device, a job for transferring the container from the first peripheral device to the second peripheral device after the process using the first peripheral device. As a result, a job may be generated having a shorter work time than when the container is caused to retreat to the main rack 7 each time a process using a peripheral device is carried out.

Figure 20:
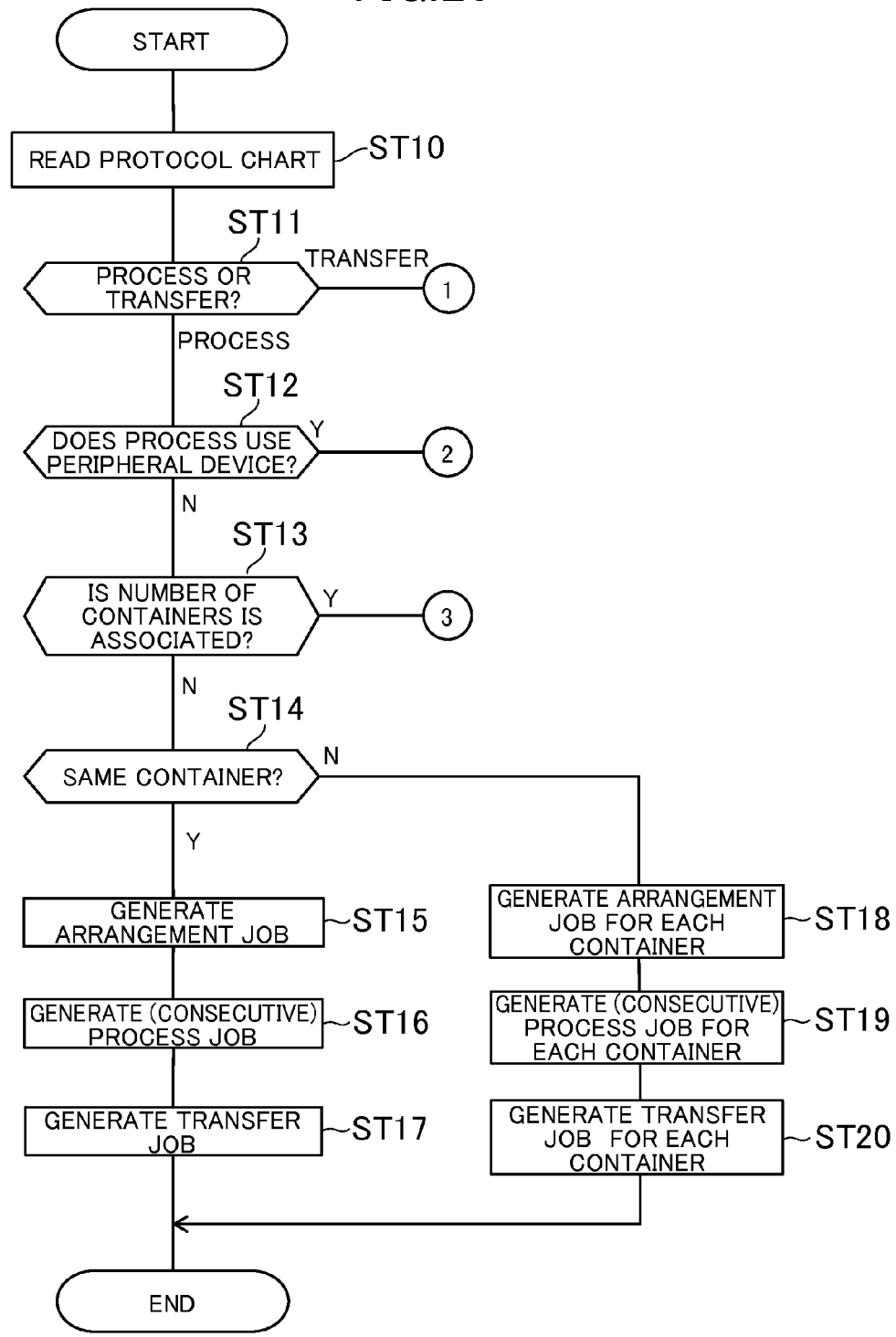
FIG. 20 is a first flowchart for illustrating operations of an operation command generation unit according to the embodiment of the present invention.

FIG. 20 is a first flowchart for illustrating operations of the operation command generation unit 12 according to this embodiment.

First, in Step ST10, the operation command generation unit 12 reads the protocol chart acquired by the protocol chart acquisition unit 11. Then, in Step ST11, the operation command generation unit 12 determines whether a process symbol or a transfer symbol is written in the read protocol chart. The protocol chart is a chart that describes the processes to be carried out on the container. Therefore, any one of a process symbol and a transfer symbol is written in the protocol chart. A protocol chart that does not include either one of a process symbol or a transfer symbol does not show a protocol at all. Therefore, when the protocol chart does not include either one of a process symbol or a transfer symbol, an error message may be displayed. Note that, when both a process symbol and a transfer symbol are written in the protocol chart, those symbols are read in the order according to the procedure line. Further, a plurality of process symbols and transfer symbols may be written.

When a process symbol is written in the protocol chart, in Step ST12, the operation command generation unit 12 determines whether or not the process symbol represents a process using a peripheral device. When the process symbol represents a process using a peripheral device, in Step ST13, the operation command generation unit 12 determines whether or not a number-of-containers symbol is associated with the process symbol.

When a number-of-containers symbol is not associated with the process symbol (when the process symbol represents a process to be carried out on a single container), in Step ST14, the same-container determination unit 16 determines whether or not the process symbol(s) represent process(es) to be carried out on the same container. In this case, when there is only one process symbol, it is immediately determined that the process symbol is a process to be carried out on the same container. On the other hand, when there are a plurality of process symbols, a determination by the same-container determination unit 16 is necessary.

When it is determined by the same-container determination unit 16 that the one or plurality of process symbols represent processes to be carried out on the same container, in Step ST15, the arrangement job generation unit 13 generates at least one job for arranging the container in the main rack 7. Further, in Step ST16, the process job generation unit 14 generates a job for carrying out the process(es) on the container. In this case, when there are a plurality of process symbols, the process job generation unit 14 generates a job for carrying out the processes consecutively on the container. Further, in Step ST17, the transfer job generation unit 15 generates a job for transferring the container to the subrack 5 at least before a process is carried out on a different container.

When it is determined in Step ST14 by the same-container determination unit 16 that the plurality of process symbols do not represent processes to be carried out on the same container, in Step ST18, the arrangement job generation unit 13 generates, for each container, a job for arranging the container in the main rack 7. Further, in Step ST19, the process job generation unit 14 generates, for each container, a job for carrying out the process on the container. In this case, when a plurality of process symbols are written for the same container, the process job generation unit 14 may generate a job for consecutively carrying out the processes on the container. In addition, in Step ST20, the transfer job generation unit 15 generates, for each container, a job for transferring the container to the subrack 5.

Figure 21:
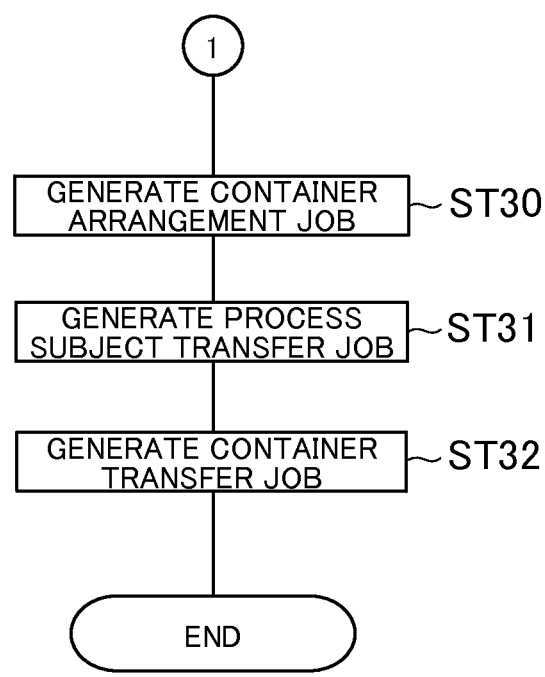
FIG. 21 is a second flowchart for illustrating operations of the operation command generation unit according to the embodiment of the present invention.

FIG. 21 is a second flowchart for illustrating the operations of the operation command generation unit 12 according to this embodiment. In the second flowchart, the processes carried out when it is determined in Step ST11 illustrated in FIG. 20 that a transfer symbol is written in the protocol chart are illustrated.

First, in Step ST30, the operation command generation unit 12 generates, by the container arrangement job generation unit 20, a job for arranging the first container in the first row 7a of the main rack 7 and a job for arranging the second container in the second row 7b of the main rack 7. Further, in Step ST31, the process subject transfer job generation unit 21 generates a job for transferring the process subject from the first container to the second container. In addition, in Step ST32, the container transfer job generation unit 22 generates a job for transferring the first container and the second container to the subrack 5.

Figure 22:
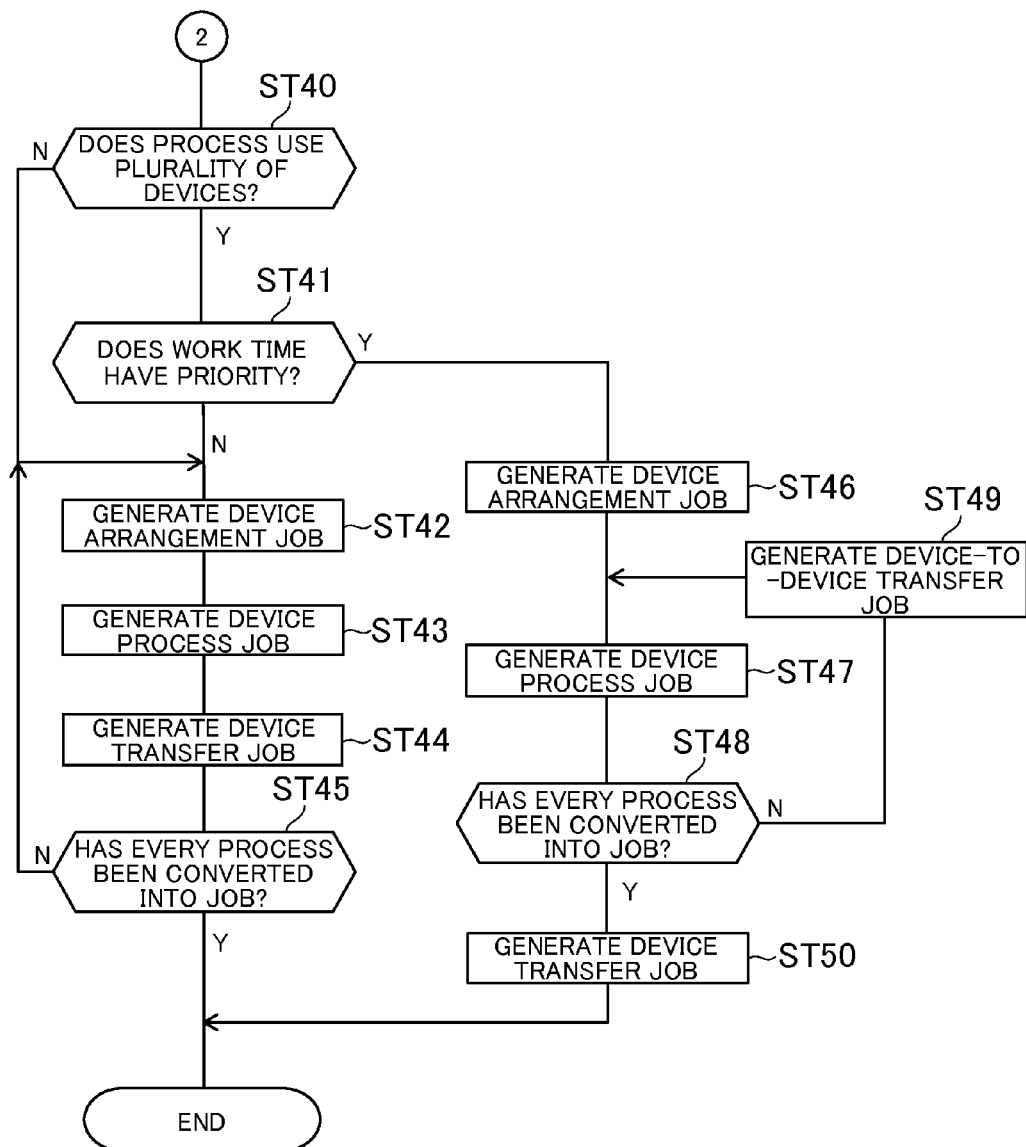
FIG. 22 is a third flowchart for illustrating operations of the operation command generation unit according to the embodiment of the present invention.

FIG. 22 is a third flowchart for illustrating the operations of the operation command generation unit 12 according to this embodiment. In the third flowchart, the processes carried out when it is determined in Step ST12 illustrated in FIG. 20 that a process symbol represents a process using a peripheral device are illustrated.

First, in Step ST40, the operation command generation unit 12 determines whether or not the process represented by the process symbol is a process using a plurality of peripheral devices. When it is determined that the process represented by the process symbol uses a plurality of peripheral devices, in Step ST41, the operation command generation unit 12 determines whether or not to give priority to shortening the work time. When it is determined not to give priority to shortening the work time (when carrying out the operations as normal by returning the container to the main rack 7 each time a process using a peripheral device is carried out), in Step ST42, the device arrangement job generation unit 14b generates a job for arranging the container in a peripheral device from the main rack 7. Further, in Step ST43, the device process job generation unit 14c generates a job for carrying out the process using a peripheral device on the container. In addition, in Step ST44, the device transfer job generation unit 14d generates a job for transferring the container from the peripheral device to the main rack 7. Then, in Step ST45, the operation command generation unit 12 determines whether or not all the process symbols representing a process using a peripheral device have been converted into a job. When a process symbol that has not been converted into a job remains, the processing performed in Step ST42 to Step ST44 is repeated. When there are no process symbols that have not been converted into a job, the processing performed by the operation command generation unit 12 is finished. Note that, when successively converting the process symbols and the like written in the protocol chart into jobs according to the procedure line, the processing may be returned to the flow illustrated in FIG. 20.

When it is determined in Step ST40 that the process represented by the process symbol is not a process using a plurality of peripheral devices, the processing of Step ST42 to Step ST44 is carried out, and then the processing performed by the operation command generation unit 12 is finished. Note that, when successively converting the process symbols and the like written in the protocol chart into jobs according to the procedure line, the processing may be returned to the flow illustrated in FIG. 20.

When it is determined in Step ST40 that the process represented by the process symbol is a process using a plurality of peripheral devices, and when it is determined in Step ST41 to give priority to shortening the work time, in Step ST46, the device arrangement job generation unit 14b generates a job for arranging the container in a peripheral device from the main rack 7. Further, in Step ST47, the device process job generation unit 14c generates a job for carrying out the process using a peripheral device on the container. In addition, in Step ST48, the operation command generation unit 12 determines whether or not all the process symbols representing a process using a peripheral device have been converted into a job. When a process symbol that has not been converted into a job remains, in Step ST49, the device-to-device transfer job generation unit 14e generates a job for transferring the container from the peripheral device at which the immediately previous process was carried out to the peripheral device at which the next process is to be carried out. Then, the processing performed in Step ST47 and Step ST48 is repeated. In Step ST48, when it is determined that there are no process symbols that have not been converted into a job, in Step ST50, the device transfer job generation unit 14d generates a job for transferring the container from the peripheral device to the main rack 7. Then, the processing performed by the operation command generation unit 12 is finished. Note that, when successively converting the process symbols and the like written in the protocol chart into jobs according to the procedure line, the processing may be returned to the flow illustrated in FIG. 20.

Figure 23:
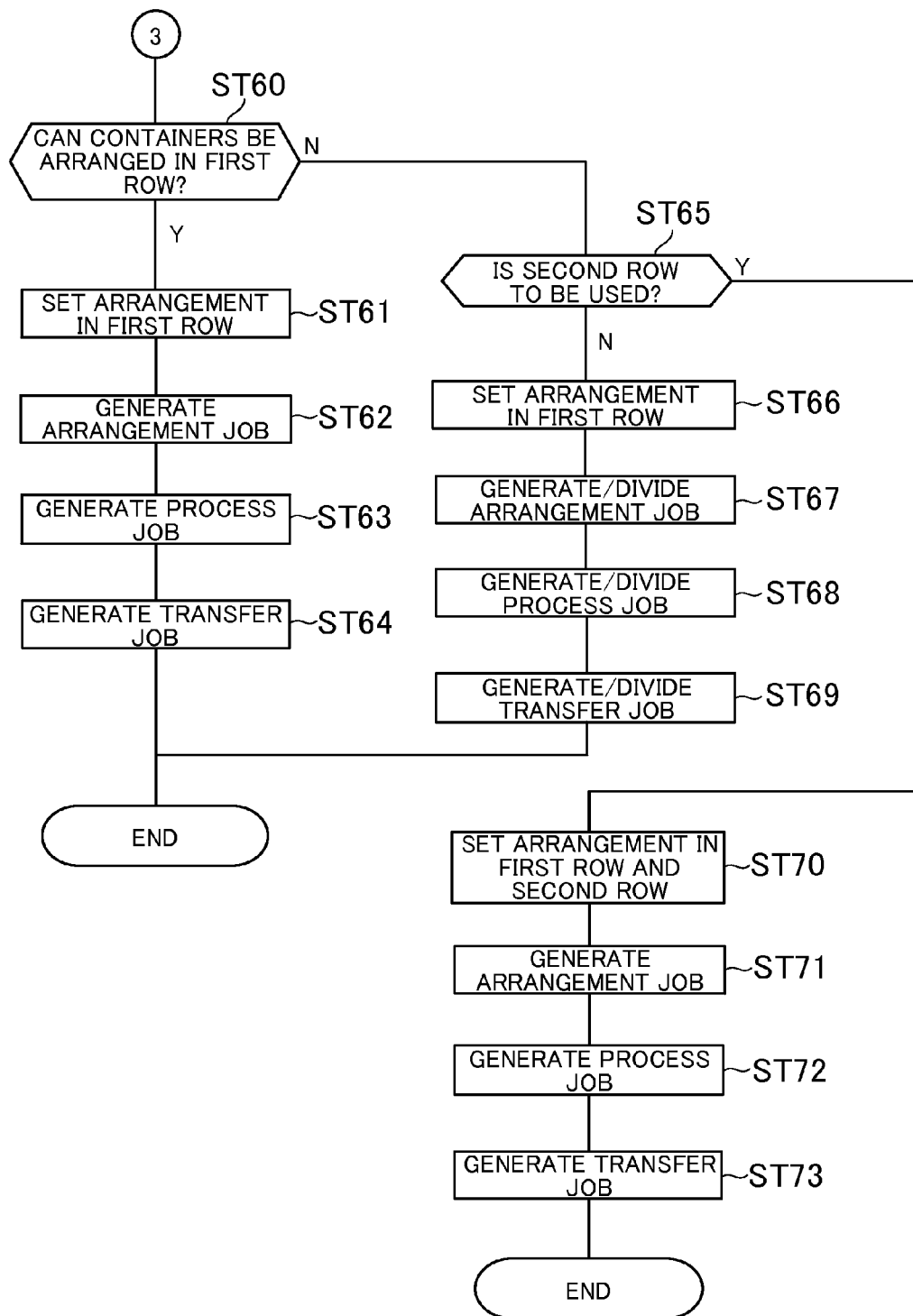
FIG. 23 is a fourth flowchart for illustrating operations of the operation command generation unit according to the embodiment of the present invention.

FIG. 23 is a fourth flowchart for illustrating the operations of the operation command generation unit 12 according to this embodiment. In the fourth flowchart, the processes carried out when it is determined in Step ST13 illustrated in FIG. 20 that a number-of-containers symbol is associated with the process symbol are shown.

First, in Step ST60, the operation command generation unit 12 determines, by the arrangement possibility determination unit 19, whether or not all of the number of containers extracted by the number-of-containers extraction unit can be arranged in the first row 7a of the main rack 7. When it is determined that all of the containers can be arranged in the first row 7a, in Step ST61, the arrangement setting unit 18 sets the arrangement of the containers in the first row 7a so that the containers are not duplicately arranged in the same storage area. Then, in Step ST62, the arrangement job generation unit 13 generates a job for arranging all of the containers in the first row 7a of the main rack 7 based on the setting of the arrangement setting unit 18. Next, in Step ST63, the process job generation unit 14 generates a job for repeating the process represented by the process symbol on all of the containers. In addition, in Step ST64, the transfer job generation unit 15 generates a job for transferring all of the containers to the subrack 5. Then, the processing performed by the operation command generation device 1 is finished. Note that, when successively converting the process symbols and the like written in the protocol chart into jobs according to the procedure line, the processing may be returned to the flow illustrated in FIG. 20.

When it is determined in Step ST60 by the arrangement possibility determination unit 19 that not all of the number of containers extracted by the number-of-containers extraction unit can be arranged in the first row 7a of the main rack 7, in Step ST65, the arrangement possibility determination unit 19 determines whether or not a container is to be stored in the second row 7b of the main rack 7. When it is determined that a container is not to be stored in the second row 7b of the main rack 7, in Step ST66, the arrangement setting unit 18 sets the arrangement of the containers in the first row 7a so that the containers are not duplicately arranged in the same storage area, and also sets so that even the containers that could not be arranged at one time in the first row 7a are not duplicately arranged in the same storage area of the first row 7a. Then, in Step ST67, the arrangement job generation unit 13 and the arrangement job division unit 13a generate, based on the setting of the arrangement setting unit 18, two or more jobs for arranging in the first row 7a of the main rack 7 the number of containers capable of being stored in the first row 7a of the main rack 7. Next, in Step ST68, the process job generation unit 14 and the process job division unit 14a generate two or more jobs for repeating the process represented by the process symbol on the number of containers capable of being stored in the first row 7a of the main rack 7. In addition, in Step ST69, the transfer job generation unit 15 and the transfer job division unit 15a generate two or more jobs for transferring to the subrack 5 the number of containers capable of being stored in the first row 7a of the main rack 7. Then, the processing performed by the operation command generation device 1 is finished. Note that, when successively converting the process symbols and the like written in the protocol chart into jobs according to the procedure line, the processing may be returned to the flow illustrated in FIG. 20.

When it is determined in Step ST65 that a container is to be stored in the second row 7b of the main rack 7, in Step ST70, the arrangement setting unit 18 sets the arrangement of the containers in the first row 7a and the arrangement of the containers in the second row 7b so that the containers are not duplicately arranged in the same storage area. Then, in Step ST71, the arrangement job generation unit 13 generates jobs for arranging all of the containers in the first row 7a and second row 7b of the main rack 7 based on the setting of the arrangement setting unit 18. Next, in Step ST63, the process job generation unit 14 generates a job for repeating the process represented by the process symbol on all of the containers. In addition, in Step ST64, the transfer job generation unit 15 generates jobs for causing all of the containers to retreat to the subrack 5. Then, the processing performed by the operation command generation device 1 is finished. Note that, when successively converting the process symbols and the like written in the protocol chart into jobs according to the procedure line, the processing may be returned to the flow illustrated in FIG. 20. Further, in the case where it is determined that not all of the containers can be stored even if the first row 7a and second row 7b of the main rack 7 are used, the arrangement job division unit 13a, the process job division unit 14a, and the transfer job division unit 15a may divide the job into two or more jobs for arranging each of the containers, jobs for carrying out the processes on the containers, and jobs for transferring the containers.

Each of the configurations in the embodiment above is described as a specific example, and the invention disclosed in this specification is not intended to be limited to those specific configurations themselves. Various modifications may be made by a person skilled in the art to the disclosed embodiment. For example, the functions, the operation method, and the like may be appropriately changed and added. Further, the control illustrated in the first to fourth flowcharts may also be appropriately replaced by one having the same functions. It is intended that the technical scope of the invention disclosed in this specification cover all such modifications. It should be understood by those skilled in the art that various modifications, combinations, sub-combinations and alterations may occur depending on design requirements and other factors insofar as they are within the scope of the appended claims or the equivalents thereof.

What is claimed is:

1. An operation command generation device configured to generate an operation command, which is a collection of jobs to be carried out by a process system comprising at least a robot based on a protocol chart comprising at least a process symbol representing a process to be carried out on a container containing a process subject, the operation command generation device comprising:
    a process job generation unit configured to generate, based on the process symbol, a job for causing the process system to carry out the process on the container at a work area;
    a transfer job generation unit configured to generate, when the process represented by the process symbol is not a process to be carried out on at least the same container, a job for causing the process system to transfer the container from the work area to a retreat area after the process represented by the process symbol has been carried out, and
    the transfer job generation unit further configured not to generate the job when the process represented by the process symbol is a process to be carried out on the same container at the work area such that the same container stays at the work area during different consecutive processes.

2. The operation command generation device according to claim 1, further comprising a same-container determination unit configured to determine whether or not a plurality of the process symbols represent processes to be carried out on the same container,
    wherein the process job generation unit and the transfer job generation unit are configured to generate, when it is determined by the same-container determination unit that the plurality of the process symbols do not represent processes to be carried out on the same container, a job for each of the containers.

3. The operation command generation device according to claim 2, wherein when it is determined by the same-container determination unit that the plurality of the process symbols represent processes to be carried out on the same container,
    the process job generation unit is configured to generate a job for causing the process system to consecutively carry out the processes represented by the plurality of the process symbols on the container, and
    the transfer job generation unit is configured to generate a job for causing the process system to transfer the container from the work area to the retreat area at least after a final process among the processes represented by the plurality of the process symbols has been carried out.

4. The operation command generation device according to claim 1, further comprising a number-of-containers extraction unit configured to extract, based on the protocol chart, a number of containers associated with the process symbol,
    wherein the process job generation unit is configured to generate, based on the process symbol, for each of the number of containers extracted by the number-of-containers extraction unit, a job for causing the process system to repeat the process to be carried out on the container, and
    wherein the transfer job generation unit is configured to generate, for each of the number of containers extracted by the number-of-containers extraction unit, a job for causing the process system to transfer the container from the work area to the retreat area.

5. The operation command generation device according to claim 4,
    wherein the work area comprises a first range in which at least one of the containers is arrangeable,
    wherein the operation command generation device further comprises an arrangement possibility determination unit configured to determine whether or not all of the number of containers extracted by the number-of-containers extraction unit are arrangeable in the first range,
    wherein the process job generation unit comprises a process job division unit configured to divide, when it is determined by the arrangement possibility determination unit that not all of the containers are arrangeable in the first range, the job for causing the process system to carry out the process represented by the process symbol into two or more jobs to be each carried out for the number of containers that are arrangeable in the first range, and wherein the transfer job generation unit comprises a transfer job division unit configured to divide, when it is determined by the arrangement possibility determination unit that not all of the containers are arrangeable in the first range, the job for causing the process system to transfer the container into two or more jobs based on the division by the process job division unit.

6. The operation command generation device according to claim 1, wherein the work area comprises a transfer source range and a transfer destination range in each of which at least one of the containers is arrangeable, and wherein the operation command generation device further comprises:

a container arrangement job generation unit configured to generate a job for causing the process system to arrange a first container containing the process subject in the transfer source range, and arrange a second container in the transfer destination range; and a process subject transfer job generation unit configured to generate, based on a transfer symbol contained in the protocol chart, a job for causing the process system to transfer the process subject from the first container to the second container.

7. The operation command generation device according to claim 1, further comprising:

a device process job generation unit configured to generate, based on the process symbol, a job for causing the process system to carry out a process using a peripheral device on the container; and a device transfer job generation unit configured to generate, when the process represented by the process symbol is not a process to be carried out on at least the same container, a job for causing the process system to transfer the container from the peripheral device to the work area after the process represented by the process symbol has been carried out.

8. The operation command generation device according to claim 7, further comprising a device-to-device transfer job generation unit configured to generate a job to be carried out between a process using a first peripheral device and a process using a second peripheral device, the processes being represented by a plurality of the process symbols, the job causing the process system to transfer the container from the first peripheral device to the second peripheral device.

9. The operation command generation device according to claim 5, wherein the work area further comprises a second range in which a plurality of the containers are arrangeable, and wherein when it is determined by the arrangement possibility determination unit that not all of the containers are arrangeable in the first range, the process job generation unit is configured to generate, based on the process symbol, a job for causing the process system to carry out the process on the container in the first range and in the second range, and the transfer job generation unit is configured to generate a job for causing the process system to transfer the container from the first range and the second range to the retreat area after the process represented by the process symbol has been carried out.

10. A non-transitory computer-readable storage medium storing a computer program for causing a computer to function as the operation command generation device of claim 1.

11. An operation command generation method for generating an operation command, which is a collection of jobs to be carried out by a process system comprising at least a robot based on a protocol chart comprising at least a process symbol representing a process to be carried out on a container containing a process subject, the operation command generation method comprising:

generating, based on the process symbol, a job for causing the process system to carry out the process on the container at a work area; and generating, when the process represented by the process symbol is not a process to be carried out on at least the same container, a job for causing the process system to transfer the container from the work area to a retreat area after the process represented by the process symbol has been carried out, wherein the job is not generated when the process represented by the process symbol is a process to be carried out on the same container at the work area such that the same container stays at the work area during different consecutive processes.

12. A process system, comprising:

the operation command generation device of claim 1;

a robot controller configured to control a control subject based on an operation command generated by the operation command generation device; and a robot configured to carry out a process on a container containing a process subject, the robot being controlled by the robot controller.

13. An operation command generation device configured to generate an operation command, which is a collection of jobs to be carried out by a process system comprising at least a robot based on a protocol chart comprising at least a process symbol representing a process to be carried out on a container containing a process subject, the operation command generation device comprising:

a process job generation means for generating, based on the process symbol, a job for causing the process system to carry out the process on the container at a work area; and a transfer job generation means for generating, when the process represented by the process symbol is not a process to be carried out on at least the same container, a job for causing the process system to transfer the container from the work area to a retreat area after the process represented by the process symbol has been carried out, wherein the transfer job generation means is further configured not to generate the job when the process represented by the process symbol is a process to be carried out on the same container at the work area such that the same container stays at the work area during different consecutive processes.

* * * * *